(12) United States Patent
Sims

(10) Patent No.: US 7,166,568 B1
(45) Date of Patent: Jan. 23, 2007

(54) COMPOSITIONS AND METHODS TO INHIBIT FORMATION OF THE C5B-9 COMPLEX OF COMPLEMENT

(75) Inventor: Peter J. Sims, Mequon, WI (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 997 days.

(21) Appl. No.: 09/020,393

(22) Filed: Feb. 9, 1998

(51) Int. Cl.
*A61K 38/36* (2006.01)
*A61K 38/17* (2006.01)
*A61K 38/00* (2006.01)
*C07K 14/435* (2006.01)

(52) U.S. Cl. .............................. 514/2; 514/8; 530/300; 530/350

(58) Field of Classification Search ............. 424/130.1, 424/140.1, 141.1, 158.1; 530/387.1, 388.2
See application file for complete search history.

(56) References Cited

U.S. PATENT DOCUMENTS

| | | | |
|---|---|---|---|
| 3,625,214 A | 12/1971 | Higuchi | |
| 4,244,946 A | 1/1981 | Rivier et al. | |
| 4,305,872 A | 12/1981 | Johnston et al. | |
| 4,316,891 A | 2/1982 | Guillemin et al. | |
| 4,447,415 A | 5/1984 | Rock | |
| 4,629,784 A | 12/1986 | Stammer | |
| 4,695,460 A | 9/1987 | Holme | |
| 4,789,734 A | 12/1988 | Pierschbacher | |
| 4,792,525 A | 12/1988 | Ruoslahti et al. | |
| 4,906,474 A | 3/1990 | Langer et al. | |
| 4,916,219 A | 4/1990 | Linhardt et al. | |
| 4,925,673 A | 5/1990 | Steiner et al. | |
| 5,135,916 A | 8/1992 | Sims et al. | |
| 5,550,108 A * | 8/1996 | Sims et al. | |
| 5,573,940 A | 11/1996 | Sims et al. | |
| 5,612,895 A | 3/1997 | Balaji et al. | |
| 5,624,837 A | 4/1997 | Fodor et al. | |
| 5,843,884 A * | 12/1998 | Sims | 514/2 |

FOREIGN PATENT DOCUMENTS

| | | |
|---|---|---|
| EP | 0351313 | 7/1989 |
| EP | 0394035 | 4/1990 |
| WO | WO 93/01286 | 1/1993 |
| WO | WO 95/23856 A1 | 9/1995 |
| WO | WO 97/17987 | 5/1997 |

OTHER PUBLICATIONS

Agrawal, et al., "Oligodeoxynucleoside phosphoramidates and phosphorothioates as inhibitors of human immunodeficiency virus," *Proc. Natl. Acad. Sci. USA* 85(19):7079-7083 (1988).
Allen, et al., "The Cambridge Crystallographic Data Centre: Computer-Based Search, Retrieval, Analysis and Display of Information," *Acta Cryst.* B35:2331-2339 (1979).
Amies, "The Use of Topically Formed Calcium Alginate as a Depot Substance in Active Immunisation" *J. Path. Bact.* 77:435-442 (1959).
Ando, et al., "The Secretory Release Reaction Initiated by Complement Proteins C5b-9 Occurs Without Platelet Aggregation Through Glycoprotein II-b-IIIa," *Blood* 73(2):462-467 (1989).
Ando, et al., "Complement Proteins C5b-9 Initiate Secretion of Platelet Storage Granules without Increased Binding of Fibrinogen or von Willebrand Factor to Newly Expressed Cell Surface GPIIb-IIIa," *J. Biol. Chem.* 263(24):11907-11914 (1988).
Archakov, et al., *Vestn. Ross. Akad. Med. Nauk.* 1:60-63 (1996).
Askew, et al., "Molecular recognition with Convergent Functional Groups" *J. Am. Chem. Soc.*, 111:1082-1090 (1989).
Bevers, et al., al. "Defective Ca2+–Induced microvesiculation and deficient Expression of Procoagulant Activity in Erythrocytes From a patient with a Bleeding Disorder" A Study of the Red Blood Cells of Scott Syndrome *Blood* 79(2): 380-388 (1992).
Blaas, et al., Paroxysmal Nocturnal Hemoglobinuria *J. Immunology* 140:3045-3051 (1988).
Bodian, et al., al., "Mutational Analysis of the Active Site and Antibody Epitopes of the Complement-inhibitory Glycoprotein CD59," *J. Exp. Med.* 185(3):507-516 (1997).

(Continued)

Primary Examiner—Phillip Gambel
(74) Attorney, Agent, or Firm—Fulbright & Jaworski

(57) ABSTRACT

Compounds modulating CD59 mediated complement activity, compositions including these compounds, and methods of making and using the compounds are disclosed, which are based on the identification of the hu CD59 amino acid residues which serve as the binding site for CD59-C9 interactions. These residues correspond to amino acid residues 42–58, and bind to the region of C9 corresponding to human 334–418, more specifically, between amino acid residues 359 and 384. Compounds can be derived using this basic amino acid sequence and corresponding three dimensional structure within the protein using any of several techniques known to those skilled in the art, including rational drug design using computer data bases and modeling of peptide/protein-ligand binding, antibodies and anti-idiotypic antibodies generated to the proteins or peptides containing this peptide sequence, and modified peptides. Those compounds imitating the structure and/or function of the peptide region are referred to herein as "peptidomimetics", and include small molecules which present the surface exposed side chains in these amino acids in the same relative positions, compounds identified by combinatorial chemistry techniques which bind to the active portions of human C9, as well as modified peptides. The compounds can be used to inhibit complement by binding to C9 analogously to CD59, or to maintain complement inhibition, by blocking CD59 binding to C9. The compounds can be administered locally or systemically in any suitable carrier in an amount effective to either inhibit complement or block the inhibition of complement, in a patient in need of treatment thereof.

18 Claims, 15 Drawing Sheets

OTHER PUBLICATIONS

Braga, et al. "A Monoclonal Antibody to the Galactose-Specific Adhesin Abrogates the resistance of *E. histolytica* to Lysis by Human Complement C5b-9" *XIV International Complement Workshop* Cambridge, U.K. (1991).

Brint, "Upperbound procedures for the identification of similar three-dimensional chemical structures," *J. Comput.-Aided Mol. Design* 2:311-310 (1988).

Burgess, et al., "Possible Dissociation of the Heparin-binding and Mitogenic Activities of Heparin-binding (Acidic Fibroblast) Growth Factor-1 from its Receptor-bind Activities by Site-directed Mutagenesis of a Single Lysine Residue," *J. Cell Biology* 111:2129-2138 (1990).

Chang, et al. "Identity of a Peptide Domain of Human C9 That Is Bound by the Cell-surface Complement Inhibitor, CD59," *J. Biol. Chem.* 269(42):26424-26430 (1994).

Clackson, et al., "Making antibody fragments using phage display libraries," *Nature* 352:624-688 (1991).

Cooper, et al., "A novel approach to molecular similarity," *J. Comput.-Aided Mol. Design* 3:253-259 (1989).

Cross, "Glycolipid Anchoring of Plasma Membrane Proteins" *Annu. Rev. Cell Biol.* 6:1-39 (1990).

Daugherty, et al., "Polymerase chain reaction facilitates the cloning, CDR-grafting, and rapid expression of a murine monoclonal antibody directed against the CD18 component of leukocyte integrins," *Nucl. Acids Res.* 19(9):2471-2476 (1991).

Davies, et al., "CD59, An LY-6-Like Protein Expressed in Human Lymphoid Cells, Regulates the Action of the Complement Membrane Attack Complex on Homologous Cells," *J. Exp. Med.* 170(3):637-654 (1989).

Davies, et al. "Membrane Defense against Complement Lysis: The Structure and Biological Properties of CD59," *Immunol. Res.* 12(3):258-275(1993).

Dupuis, et al., "Mutations in the Putative Lipid-Interaction Domain of Complement C9 Result in Defective Secretion of the Functional Protein," *Mol. Immunol.* 30(1):95-100 (1993).

Fletcher, et al., "Sequence-specific $^1$H-NMR assignments and folding topology of human CD59," *Protein Sci.* 2:2015-2027 (1993).

Fletcher, et al., "Structure of soluble, glycosylated form of the human complement regulatory protein CD59," *Structure* 2:185-199 (1994).

Gerber, et al., "Phosphatidylinositol Glycan (PI-G) Anchored Membrane Proteins," *J. Biol. Chem.* 267(17):12168-12173 (1992).

Ghoshal, et al., "Computer Aids in Drug Design—Highlights" *Pol. J. Pharmacol.* 48(4): 359-377 (1996).

Gilbert, et al. "Platelet-derived Microparticles Express High Affinity Receptors for Factor VIII" *J. Biol. Chem* 266(8): 1-8 (1991).

Gregoriadis, "Liposomes," in *Drug Carriers in Biology and Medicine*, Chap. 14, pp. 287-341 (Academic Press, 1979).

Groux, et al., "A 19-kDa Human Erythrocyte Molecule H19 is Involved in Rosettes, Present on Nucleated Cells, and Required for T Cell Activation," *J. Immunology* 142(9):3013-3020 (1989).

Hahn, et al. "Overlapping But Nonidentical Binding Sites on CD2 for CD58 and a second Ligand CD59" *Science* 256: 1805-1807 (1992).

Hamilton, et al. "The Terminal Complement Proteins C5b-9 Augment Binding of High Density Lipoprotein and its Apolipoproteins A-I and A-Ii to Human Endothelial Cells" *J. Clin. Invest* 88: 1833-1840 (1991).

Hamilton, et al., "Complement Proteins C5b-9 Induce Vesiculation of the Endothelial Plasma Membrane and Expose Catalytic Surface for Assembly of the Prothrombinase Enzyme Complex" *J. Bio. Chem.*, 265:3809-3814 (1990).

Hamilton, et al., "Regulatory Control of the Terminal Complement Proteins at the Surface of Human Endothelial Cells: Neutralization of a C5b-9 Inhibitor by Antibody to CD59," *Blood* 76(12):2572-2577 (1990).

Hamilton, et al, "Regulatory Control of he Terminal Proteins at the Surface of Human Endothelial Cells: Neutralization of a C5b-9 Inhibitor by Antibody to CD59," *Blood* 76(12): 2572-2577 (1990).

Hansch, et al. "Paroxysmal Nocturnal Hemoglobinuria Type III" *J. Clin. Invest.* 80:7-12 (1987).

Hansch, et al., "Release of C8 Binding Protein (C8bp) From the Cell Membrane by Phosphatidylinositol-Specific Phospholipsae C," *Blood* 72(3):1089-1092 (1988).

Harada, et al., "Monochronal antibody G6K12 specific for membrane-associated differentiation marker of human stratified squamous epithelia and squamous cell carcinoma," *J. Oral Pathol. Med.* (Denmark), 22(4):145-152 (1993).

Hatanaka, et al., "The functions of the ninth component of human complement are sustained by disulfide bonds with different susceptibilities to reduction," *Biochim. Biophys. Acta Protein Struct. Mol. Enzymol.* 1209(1):117-122 (1994).

Hattori, et al. "Complement Proteins C5b-9 Induce Secretion of High Molecular Weight Multimers of Endothelial von Willebrand Factor and Translocation of Granule Membrane Protein GMP-140 to the Cell Surface," *J. Biol. Chem.* 264(15):9053-9060 (1989).

Hattori, et al., "Stimulated Secretion of Endothelial von Willebrand Factor Is Accompanied by Rapid Redistribution to the Cell Surface of the Intracellular Granule Membrane Protein GMP-140" *J. Bio. Chem.*, 264(14):7768-7771 (1989).

Holguin, et al., "Isolation and Characterization of a Membrane Protein from Normal Human Erythrocytes That Inhibits Reactive Lysis of the Erythrocytes of Paroxysmal Nocturnal Hemoglobinuria," *J. Clin. Invest.* 84(1):7-17 (1989).

Houle, et al., "Evidence for restriction of the ability of complement to lyse homologous Erythrocytes," *J. Immunol.* 133:1444-1452 (1984).

Houle, et al., "Restriction of Cell Lysis by Homologous Complement: II. Protection of Erythrocytes Against Lysis by Newly Activated Complement," *Blood* 71(2):287-292 (1988).

Huang et al., "Development of a Common 3D Pharmacophore for Delta-Opioid Recognition From Peptides and Non-Peptides Using a Novel Computer Program" *J. Comput. Aided Mol. Des.* 11(1):21-78 (1997).

Husler, et al., "Chimeras of Human Complement C9 Reveal the Site Recognized by Complement Regulatory Protein CD59," *J. Biol. Chem.* 270(8):3483-3486 (1995).

Husler, et al., "Role of a Disulfide-bonded Peptide Loop within Human Complement C9 in the species-Selectivity of Complement Inhibitor CD59", *Biochem.*, 35(10):3263-3269 (1996).

Inai, et al., "Immunohistochemical detection of an enamel protein-related epitope in rat bone at an early stage of osteogenesis," *Histochemistry* (Germany), 99(5):335-362 (1993).

Itakura, et al., "Synthesis and Use of Synthetic Oligonucleotides," in *Ann. Rev. Biochem.* 53:323-356 (1984).

Kieffer, et al., "Three-Dimensional Solution Structure of the Extracellular Region of the Complement Regulatory Protein CD59, a New Cell-Surface Protein Domain Related to Snake Venom Neurotoxins," *Biochemistry* 33:4471-4482 (1994).

Kinoshita, et al., "Defective Glycosyl Phosphatidylinositol Anchor Synthesis and Paroxysmal Nocturnal Hemoglobinuria," *Adv. Immunol.* 60:57-103 (1995).

Kleinberg, et al., "New Approaches and Technologies in Drug Design and Discovery" *Am. J. Health Syst. Pharm.* 52(12):1323-1336 (1995).

Kooyman, et al. "In Vivo Transfer of GPI-Linked Complement Restriction Factors from Erythrocytes to the Endothelium" *Science* 269:89-92 (1995).

Korty, et al. "CD59 Functions as a Signal-Transducing Molecule for Human T Cell Activation" *J. Immunol.* 146:4092-4098 (1991).

Kubinyi, "Strategies and Recent Technologies in Drug Discovery" *Pharmazie* 50(10):647-662 (1995).

Lazar, et al., "Transforming Growth Factor :Mutation of Aspartic Acid 47 and Leucine 48 Results in Different Biological Activities," *Molecular and Cellular Biology* 8(3): 1247-1252 (1988).

Lewis, et al., "Automated site-directed drug design: the concept of spacer skeletons for primary structure generation," *Proc. R. Soc. Lond.*, 236(1283):125-140 (1989).

Lewis, et al., "Automated site-directed drug design: the formation of molecular templates in primary structure generation," *Proc. R. Soc. Lond.*, 236(1283):141-162 (1989).

Li, et al., A computer Screening Approach to Immunoglobulin Superfamily Structures and Interactions: Discovery of Small Non- Peptidic CD4 Inhibitors and Novel Immunotherapeutics *Proc. Natl. Acad. Sci. USA* 94(1):73-78 (1997).

Lin, et al. "A family showing inheritance of the Inab phenotype" *Transfusion* 28: 427-429 (1988).

Lublin, et al., "Decay-Accelerating Factor and Membrane Cofactor Protein," *Current Topics Microbiol. Immunol.* 153:123-145 (1989).

Lybrand, "Ligand-Protein Docking and Rational Drug Design" *Curr. Opin. Struct. Biol.* 5(2):224-228 (1995).

Martin, et al., "Induction of expression of cell-surface homologous restriction factor upon anti-CD3 stimulation of human peripheral lymphocytes," *Proc. Natl. Acad. Sci. USA* 85:213-217 (1988).

McKinlay, et al., "Rational Design of Antiviral Agents," *Annual Review of Pharmacology and Toxicology*, 29:111-122 (1989).

Medof, et al., "Inhibition of Complement Activation on the Surface of Cells After Incorporation of Decay-Accelerating Factor (DAF) Into Their Membranes," *J. Exp. Med.* 160(5):1558-1578 (1984).

Merrifield, "Solid-Phase Peptide Synthesis. I. The Synthesis of a Tetrapeptide," *J. Am. Chem. Soc.* 85:2149-2154 (1964).

Mulder, et al., "Characterization of Two Human Monoclonal Antibodies Reactive with HLA-B12 and HLA-B60, Respectively, Raised by *in vitro* Secondary Immunization of Peripheral Blood Lymphocytes," *Hum. Immunol.* 36(3):186-192 (1993).

Nakano, et al., "Determination of the Active Site of CD59 with Synthetic Peptides," *Mol. Immunol.* 32(4):241-247 (1995).

Narang, et al., "Chemical Synthesis of Deoxyoligonucleotides by the Modified Triester Method," in *Methods Enzymol.* 65:610-620 (1980).

Nelson, et al., at pp. 227, 271 and 285, respectively, in *Burger's Medicinal Chemistry*, Part 1, the *Basis of Medicinal Chemistry*, 4th Edition, (Wolff, ed.) (John Wiley & Sons, NY, 1980).

Nicholson-Weller, et al., "Surface Membrane Expression by Human Blood Leukocytes and Platelets of Decay-Accelerating Factors, a Regulatory Protein of the Complement System," *Blood* 65(5): 1237-1244 (1985).

Ninomiya, et al., "The Human Complement Regulatory Protein CD59 Binds to the α-Chain of C8 and to the "b" Domain of C9," *J. Biol. Chem.* 267:13675-13680 (1992).

Ninomiya, et al. "Contribution of the N-Linked Carbohydrate of Erythrocyte Antigen CD59 to ITS Complement -inhibitory Activity" *J. Biol. Chem.* 267(12): 8404-8410 (1992).

Nose, et al. "Tissue distribution of HRF20, a novel factor preventing the membrane attack of homologous complement, and its predominant expression on endothelial cells *in vivo*" *Immunology* 70:145-149 (1990).

Offensperger, et al., "*In Vivo* inhibition of duck hepatitis B virus replication and gene expression by phosphorothioate modified antisense oligodeoxynucleotides," *EMBO J.* 12(3): 1257-1262 (1993).

Okada, et al. "Monoclonal Antibodies Capable of Causing Hemolysis of Neuraminidase-treated Human Erythrocytes by Homologous Complement" *J. Immunol.* 143: 2262-2266 (1989).

Okada, et al., "20 Kda Homologous Restriction Factor of Complement Resembles T Cell Activating Protein," *Biochem. Biphys. Res. Comm.* 162(3):1553-1559 (1989).

Okada, et al., "A novel membrane glycoprotein capable of inhibiting membrane attack by homologous complement," *International Immunology* 1(2):205-208 (1989).

Pangburn, et al., "Deficiency of an erythrocyte membrane protein with complement regulatory activity in paroxysmal nocturnal hemoglobinuria," *Proc. Natl. Acad. Sci. USA* 80:5430-5434 (1983).

Perry & Davies, *QSAR: Quantitative Structure-Activity Relationships in Drug Design* pp. 189-193 (Alan R. Liss, inc. 1989).

Petranka, et al., "Structure-Function Relationship of the Complement Regulatory Protein, CD59," *Blood Cells Mol. Dis.* 22(3):281-296 (1996).

Philbrick, et al. The CD59 antigen is a structural homologue of murine Ly-6 antigens but lacks interferon inducibility, *Eur. J. Immunol.* 20: 87-92 (1990).

Platt, et al. "Transplantation of discordant xenografts: a review of progress" *Immunology Today* 11(12): 450-457 (1990).

Ripka, "Computers Picture the Perfect Drug," *New Scientist*, 54-57 (Jun. 16, 1988).

Rollins, et al., "The Complement-Inhibitory Activity of CD59 Resides in its Capacity to Block Incorporation of C9 Into Membrane C5b-9," *J. Immunol.* 144(9):3478-3483 (1990).

Rollins, et al., "Inhibition of Homologous Complement by CD59 is Mediated by a Species-Selective Recognition Conferred Through Binding to C8 Within C5b-8 or C9 Within C5b-9," *J. Immunol.* 146(7):2345-2351 (1991).

Rotivinen, et al., "Computer-Aided Drug Design," *Acta Pharmaceutica Fennica*, 97:159-166 (1988).

Sarin, et al., "Inhibition of acquired immunodeficiency syndrome virus by oligodeoxynucleoside methylphosphonates," *Proc. Natl. Acad. Sci. USA* 85(20):7448-7794 (1989).

Schaller, et al., "Identification of the Disulfide Bonds of the Human Complement Component C9 and Comparison with the Other Terminal Components of the Membrane Attack Complex," *J. Protein Chem.* 13:472-473 (1994).

Schonermark, et al., "The C8-binding protein of human erythrocytes: interaction with the components of the complement-attack phase," *Immunology* 63(4):585-590 (1988).

Schönermark, et al., "Homologous Species Restriction in Lysis of Human Erythrocytes: A Membrane-Derived Protein with C8-Binding Capacity Functions as an Inhibitor," *J. Immunol.* 136(5):1772-1776 (1986).

Shattil, et al, "Changes in the Platelet Membrane Glycoprotein IIb-IIIa Complex during Platelet Activation," *J. Biol. Chem.* 260():11107-11112 (1985).

Shaw, et al., "Modified deoxyoligonucleotides stable to exonuclease degradation in serum," *Nucleic Acids Res.* 19(4):747-750 (1991).

Shin, et al., "Membrane Factors Responsible for Homologous Species Restriction of Complement-Mediated Lysis: Evidence for a Factor Other Than DAF Operating at the Stage of C8 and C9," *J. Immunology* 136(5):1777-1782 (1986).

Shin, et al., "Cytotoxic Action and Other Metabolic Consequences of Terminal Complement Proteins," *Prog. Allergy* 40:44-81 (1988).

Sims, "Interaction of Human Platelets with the Complement System", *Platelet Immunobiology*, Chapter 18, 354-383 (1990).

Sims, "Complement Protein C9 Labeled with Flourescein Isothiocyanate Can Be Used to Monitor C9 Polymerization and Formation of the Cytolytic Membrane Lesion" *Biochemistry* 23: 3248-3260 (1984).

Sims , et al. "The response of human platelets to activated components of the complement system" *Immunology Today* 12(9): 338-342 (1991).

Sims, et al., "Assembly of the Platelet Prothrombinase Complex Is Linked to Vesiculation of the Platelet Plasma Membrane," *J. Biol. Chem.* 264(29):17049-17057 (1989).

Sims, et al., "Complement Proteins C5b-9 Cause Release of Membrane Vesicules for the Platelet Surface That Are Enriched in the Membrane Receptor for Coagulation Factor VA and Express Prothrombinase Activity," *J. Biol. Chem.* 263(34):18205-18212 (1988).

Sims, et al., "Regulatory Control of Complement on Blood Platelets," *J. Biol. Chem.* 264(32):19228-19235 (1989).

Sims, et al., "Repolarization of the Membrane Potential of Blood Platelets After Complement Damage: Evidence for a $Ca^{++}$-Dependant Exocytotic Elimination of C5b-9 Pores," *Blood* 68(2):556-561 (1986).

Sims, "Plasma Proteins; Complement" in *Transfusion Medicine*, pp. 1582-1591, (Mintz, ed.)W.B. Saunders, Philadelphia (1994-1995).

Slanetz, et al. "Heterodimeric, disulfide-linked α/β T cell receptors in solution" *Eur. J. Immunol.* 21: 179-183 (1991).

Spatola, *Chemistry and Biochemistry of Amino Acids, Peptides, and Proteins* vol. 7, pp. 257-357, (Weistein, B, Ed.), Marcel Dekker, New York (1983).

Stauber, et al., "Rapid generation of monoclonal antibody-secreting hybridomas against African horse sickness virus by *in vitro* immunization and the fusion/cloning technique," *J. Immunol. Methods* (Netherlands), 161(2):157-168 (1993).

Stefanova, et al., "Characterization of a Broadly Expressed Human Leucocyte Surface Antigen MEM-43 Anchored in Membrane Through Phosphastidylinositol," *Molecular Immunology* 26(2):153-161 (1989).

Stewart, et al., "Orientation of Human CD59 Upon Insertion into the Phospholip Bilayer. A Fluorescent Resonance Energy Transfer Study" *Biophysical Journal* 59:48 (1991). (abstract).

Sugita, et al. "Isolation from Human Erythrocytes of a New Membrane Protein Which Inhibits the Formation of Complement Transmembrane Channels," *J. Biochem* 104: 633-637 (1988).

Szelke, et al., *In Peptides: Structure and Function, Proceedings of the Eighth American Peptide Symposium*, (Hruby, et al., eds.) pp. 579-582, (Pierce Chemical Co., Rockford, Ill. (1983).

Szostak, "*In Vitro* genetics," *TIBS* 19:89-93 (1992).

Tao, et al., "Studies of Aglycosylated Chimeric Mouse-Human IgC," *J. Immunology* 43(8):2595-2601 (1989).

Takebe, et al. "SRα Promoter: an efficient and Veratile mammalian cDNA Expression System Composed of the simian Virus 40 Early Promoter and the R-U5 Segment of Human T-Cell Leukemia Virus Type 1 Long Terminal Repeat" *Mol. Cell. Biol* 8(1): 466-472 (1988).

Taylor, et al., "The Word Wide Web as a graphical user interface to program macros for molecular graphics, molecular modeling, and structure-based drug design" *J. Mol. Graph.* 14(5):291-296 (1996).

Telen, "Identification of Human Erythrocyte Blood Group Antigens on Decay-Accelerating Factor (DAF) and an Erythrocyte Phenotype Negative for DAF" *J. Exp. Med* 167: 1993-1998 (1988).

Terstappen, et al. "Expression of the DAF (CD55) and CD59 antigens during normal hemotopoietic cell differentiation" *Journal of Leukocyte Biology* 52:652-660 (1992).

Van De Meer, et al., "Complement Proteins C5b-9 Induce Transbilayer Migration of Membrane Phospholipids," *Biophys. J.* 56:935-946 (1989).

Venkateswaran, et al., "Production of Anti-Fibroblast Growth Factor Receptor Monoclonal Antibodies by *In Vitro* Immunization," *Hybridoma* 11(6):729-739 (1992).

Weiner, et al., "A New Force Field for Molecular Mechanical Simulation of Nucleic Acids and Proteins," *J. Am. Chem. Soc.* 106(3):765-784 (1984).

Wendoloski, et al., "Biophysical Tools for Structure-Based Drug Design" *Pharmacol. Ther.* 60(2):169-183 (1993).

Wiedmer, et al. "Complement Proteins C5b-9 Stimulate Procoagulant Activity through Platelet Prothrombinase" *Blood* 68(4): 875-880 (1986).

Wiedmer, et al., "Complement C5b-9-stimulated Platelet Secretion Is Associated with a Ca2$^+$-initiated Activation of Cellular Protein Kinases," *J. Biol. Chem.* 262(28):13674-13681 (1987).

Wiedmer, et al., "On the Mechanism by Which Complement Proteins C5b-9 Increase Platelet Prothrombinase Activity," *J. Biol. Chem.* 261(31):14587-14592 (1986).

Wiedmer, et al. "Participation of Protein Kinases in Complement C5b-9 Induced Shedding of Platelet Plasma Membrane Vesicles" *Blood* 78(11):1-7 (1991).

Wiedmer, et al, "Role of Calcium and Calpain in Complement-Induced Vesiculation of the Platelet Plasma Membrane and in the Exposure of the Platelet Factor VA Receptor," *Biochemistry* 29:623-632 (1990).

Wiedmer, et al., "Effect of Complement Proteins C5b-9 on Blood Platelets," *J. Biol. Chem.* 260(13):8014-8019 (1984).

Wiedmer, et al., "Cyanine Dye Fluorescence Used to Measure Membrane Potential Changes due to the Assembly of Complement Proteins C5b-9," *J. Membr. Biol.* 84:249-258 (1985).

Wurzner, et al. "Inhibition of Terminal Complement Complex Formation and Cell Lysis by Monoclonal Antibodies" *Complement Inflamm.* 8: 328-340 (1991).

Yamashina, et al. "Inherited Complete Deficiency of 20-Kilodalton Homologous Restriction Factor (CD59) as a Cause of Paroxysmal Nocturnal Hemoglobinuria" *The New England Journal of Medicine* 323(17): 1184-1189 (1990).

Yu, et al., "Mapping the Regions of the Complement Inhibitor CD59 Responsible for Its Species Selective Activity," *Biochemistry* 36:9423-9428 (1997).

Yu, et al., "Mapping the Active Site of CD59," *J. Exp. Med.* 185(4):745-753 (1997).

Zalman, et al., "Deficiency of the Homologous Restriction Factor in Paroxysmal Nocturnal Hemoglobinuria," *J. Exp. Med.* 165:572-577 (1987).

Zalman, et al. "Isolation of a human erythrocyte membrane protein capable of inhibiting expression of homologous complement transmembrane channels," *Proc. Natl. Acad. Sci. USA* 83: 6975-6979 (1986).

Zhao, et al., "Identity of the Residues Responsible for the Species-restricted Complement Inhibitory Function of Human CD59," *J. Biol. Chemistry* 273(17):10665-10671 (1998).

* cited by examiner

```
              -25    -20    -15    -10    -5    01    5    10    15
Human                    GIQGGSVLFGLLLVLAVFCHSGHS LQCYNCPNPTADCKTAVN
                         :   :::   :  :::::       ::  :  :::  :
Rabbit   MTSRGVHLLLRLLFLLAVFYSS-DSSSLMCYHCLLPSPNCSTVTN 20    25    30    35    40    45    50    55    60
Human    CSSDFDACLITKAGLQVYNKCWKFEHCNENDVTTRLRENELTYY
         :::  :::::: :  :  :::  ::  :::  ::::::
Rabbit   CTPNHDACLTAVSGPRVYROCWRYEDCNFEFISNRLEENSLKYN 65    70    75    80    85    90    95    100
Human    CCKKDLCNFNEQLENGGTSLSEKTVLLLVTPFLAAAWSLHP
         :: ::::::           :  :::  ::::: :::::    :
Rabbit   CCRKDLCNGPEDDG---TALTGRTVLL-VAPLLAAARNLCL
```

FIG. 1A

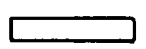
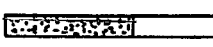
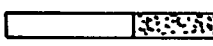
*FIG. 2A*
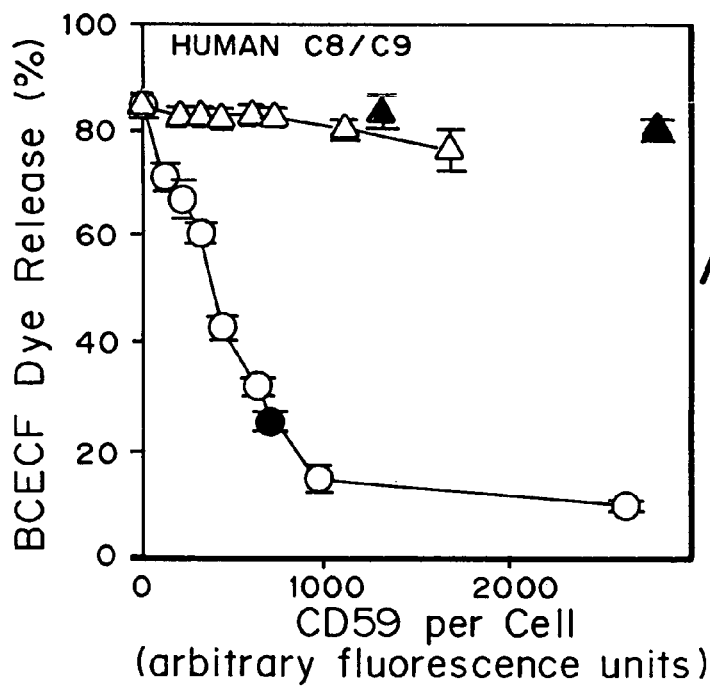
*FIG. 2B*
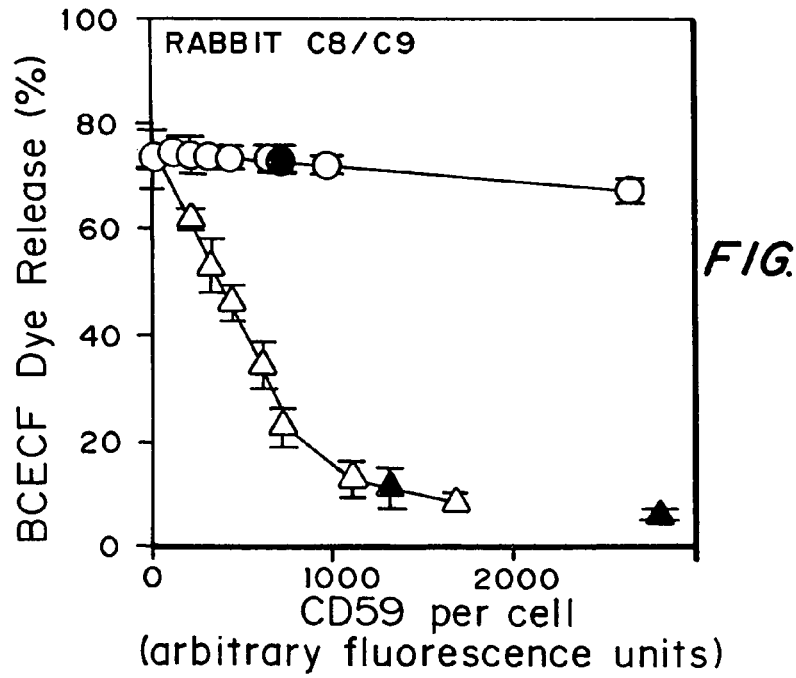
*FIG. 2C*

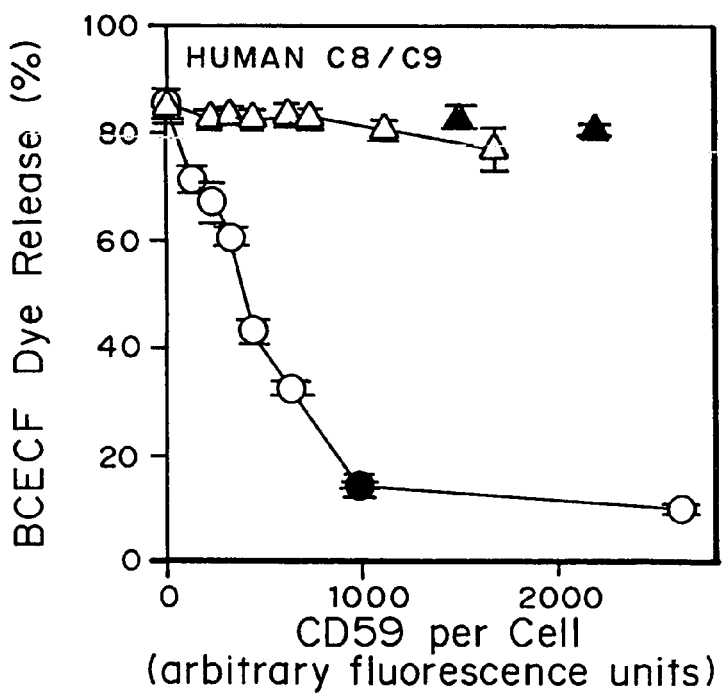
FIG. 3A
FIG. 3B
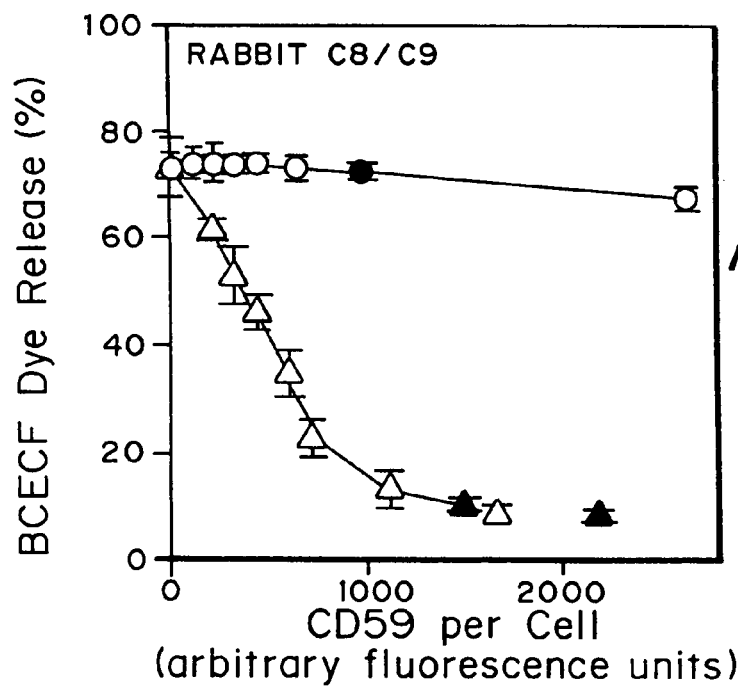
FIG. 3C

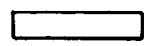
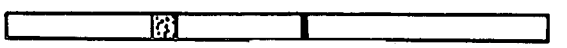
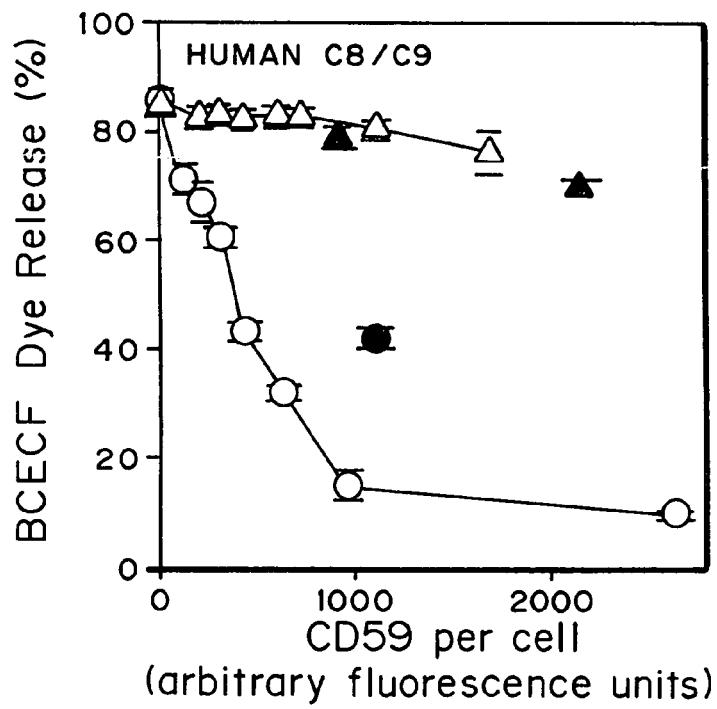
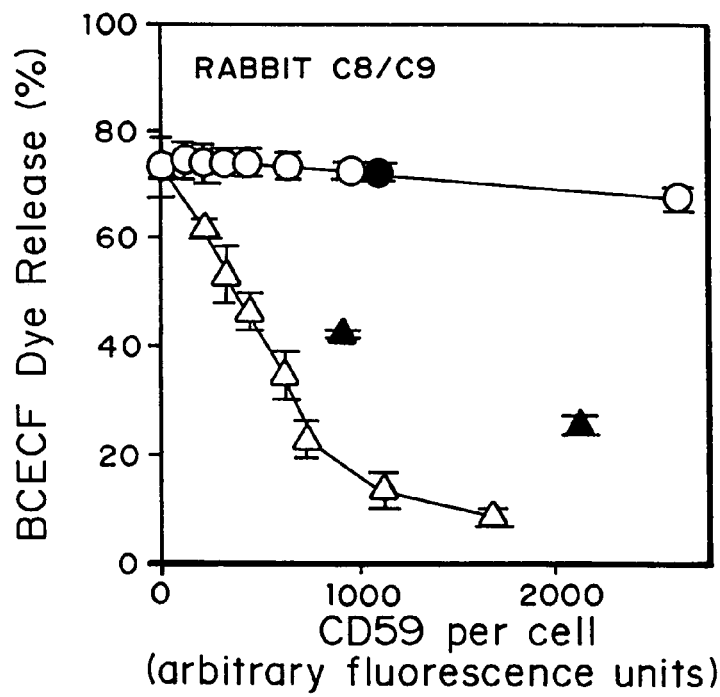

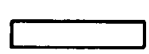
FIG. 5A
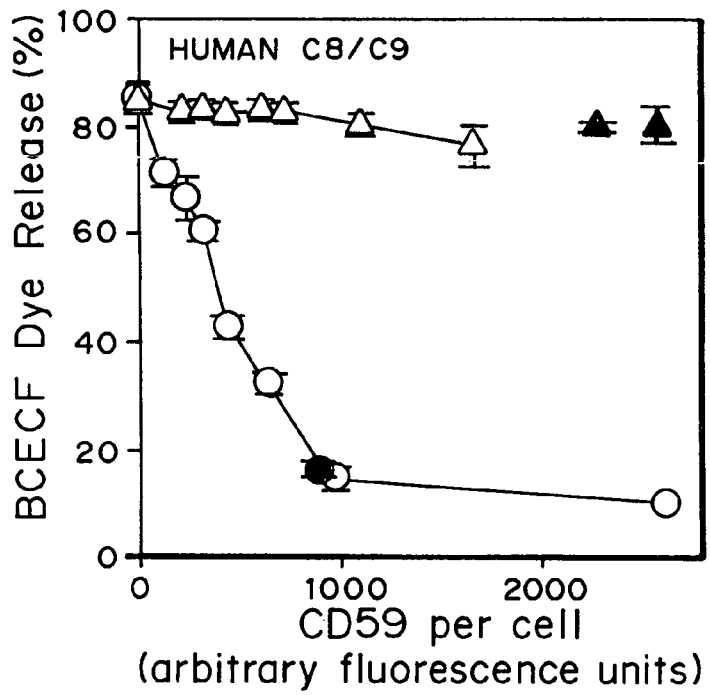
FIG. 5B
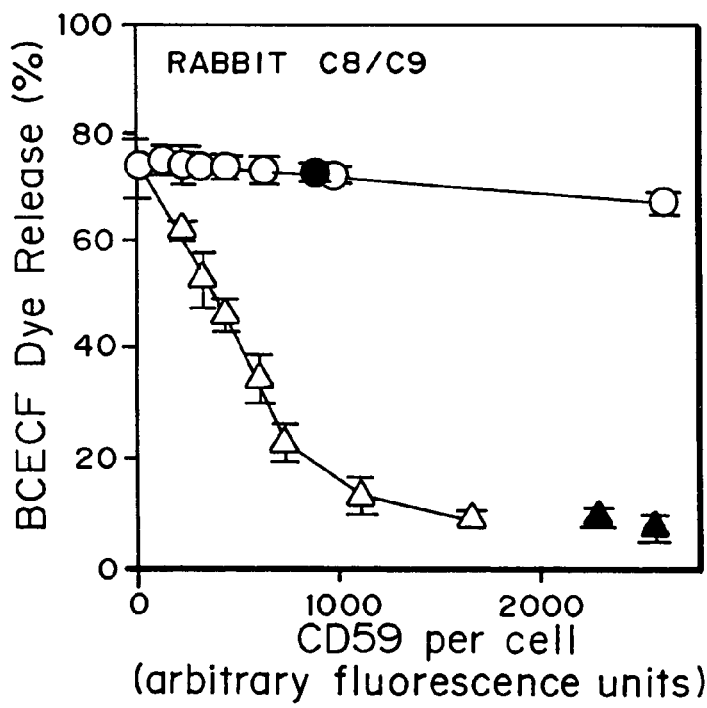
FIG. 5C

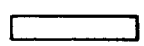
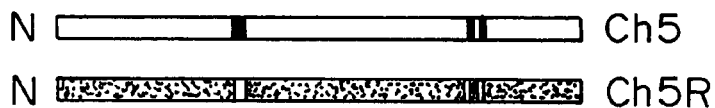
FIG. 6A
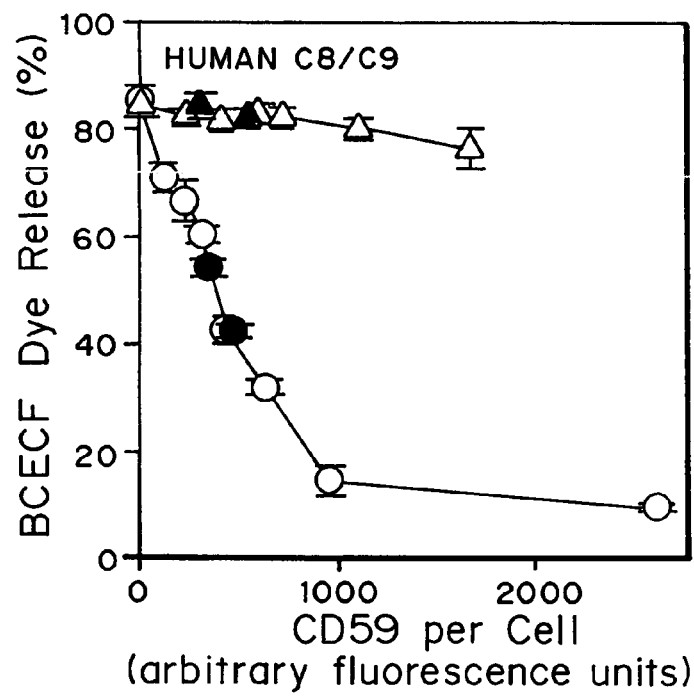
FIG. 6B
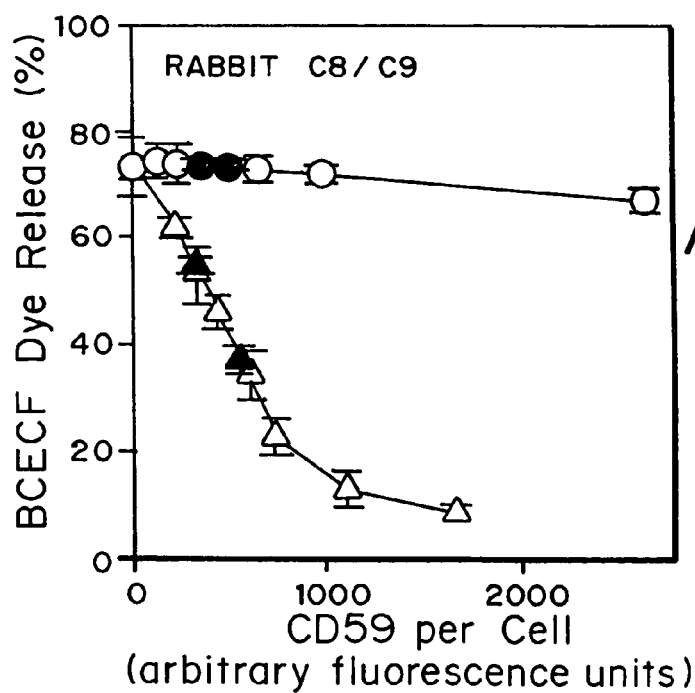
FIG. 6C

|             |   |   | 5 |   |   |   | 10 |   |   |   | 15 |   |   |   | 20 |   |   |   | 25 |   |   |   | 30 |   |   |   | 35 |   |
|-------------|---|---|---|---|---|---|----|---|---|---|----|---|---|---|----|---|---|---|----|---|---|---|----|---|---|---|----|---|
|             |   |   | * |   |   |   |    |   |   |   |    |   |   |   |    |   |   |   | *  |   |   | * |    |   | * |   | *  |   |
| Human       | L | Q | C | Y | N | C | P  | N | P | T | .  | A | D | C | K  | T | A | V | N  | C | S | S | D  | F | D | A | C  | L | I | T | K | A | G | L | Q | V | Y | N | K |
| Baboon      | L | Q | C | Y | N | C | P  | N | P | T | .  | T | N | C | K  | T | A | I | N  | C | S | S | G  | F | D | T | C  | L | I | A | R | A | G | L | Q | V | Y | N | Q |
| Afr grn mnky| L | Q | C | Y | N | C | P  | N | P | T | .  | T | D | C | K  | T | A | I | N  | C | S | S | G  | F | D | T | C  | L | I | A | R | A | G | L | Q | V | Y | N | Q |
| Owl monkey  | L | Q | C | Y | S | C | P  | Y | P | T | .  | T | Q | C | T  | M | T | T | N  | C | T | S | N  | I | D | S | C  | L | I | A | K | A | G | S | R | V | Y | Y | R |
| Marmoset    | L | Q | C | Y | S | C | P  | Y | S | T | .  | T | Q | C | T  | T | T | T | N  | C | T | S | N  | I | D | S | C  | L | I | A | K | A | G | L | R | V | Y | Y | R |
| HVS-15      | L | Q | C | Y | N | C | S  | H | S | T | .  | A | R | C | T  | T | T | T | N  | C | T | S | N  | I | D | S | C  | L | I | A | K | A | G | S | G | V | Y | Y | R |
| Pig         | L | Q | C | Y | N | C | I  | N | P | A | .  | M | Q | C | K  | T | S | T | S  | C | T | S | N  | L | D | S | C  | L | I | A | K | A | G | S | G | V | Y | N |   |
| Sheep       | L | Q | C | Y | S | C | I  | N | Q | V | .  | G | S | C | T  | X | X | M | n  | c | S | Y | N  | Q | D | A | C  | I | F | V | X | A | V | P | P | K | T |   |   |
| Rabbit      | S | L | M | C | Y | H | C  | I | I | P | S  | . | D | C | T  | S | V | I | n  | c | T | X | N  | Q | D | A | c  | L | Y |   |   |   |   |   |   |   |   |   |   |
| Rat         | L | R | C | Y | N | C | L  | D | P | V | .  | S | S | C | K  | T | N | S | T  | C | S | P | N  | L | D | A | C  | L | T | A | V | S | G | P | R | V | Y | R | Q |
| Mouse       | L | T | C | Y | H | C | F  | Q | P | V | V  | S | S | C | N  | M | N | S | T  | C | S | P | D  | Q | D | S | C  | L | Y | A | V | A | G | M | Q | V | Y | Q | R |

*FIG.8A*

|              | 40 | 45 | 50 | 55 | 60 | 65 | 70 | 71 | 75 |
|---|---|---|---|---|---|---|---|---|---|
|              |    | *  |    |    | *  |    | *  |    |    |
| Human        | CWKFEHCNFNDVTTRIRENELTYYCCKKDLCN..FNEQLEN |
| Baboon       | CWKFANCNFNDISTLIKENELQYFCCKEDLCN.....EQLEN |
| Afr grn mnky | CWKFANCNFNDISTLIKESELQYFCCKKDLCN..FNEQLEN |
| Owl monkey   | CWKFEDCTFSRVSNQLSENEIKYYCCKKNLCN..FNEALEN |
| Marmoset     | CWKFEDCTFRQLSNQLSENEIKYHCCRENLCN..FNGILEN |
| HVS-15       | CWKFDDCSFKRISNQLSETQLKYHCCKKNLCN..VNKGI   |
| Rabbit       | CWRYEDCNFEFISNRLEENSLKYNCCRKDLCN..GPEDDG  |
| Rat          | CWRFSDCNAKFIISRLEIANVQYRCCQADLCNKSFEDKPNN |
| Mouse        | CWKQSDCHGEIIMDQLEETKLKFRCCQFNLCNKSD       |

FIG. 8B

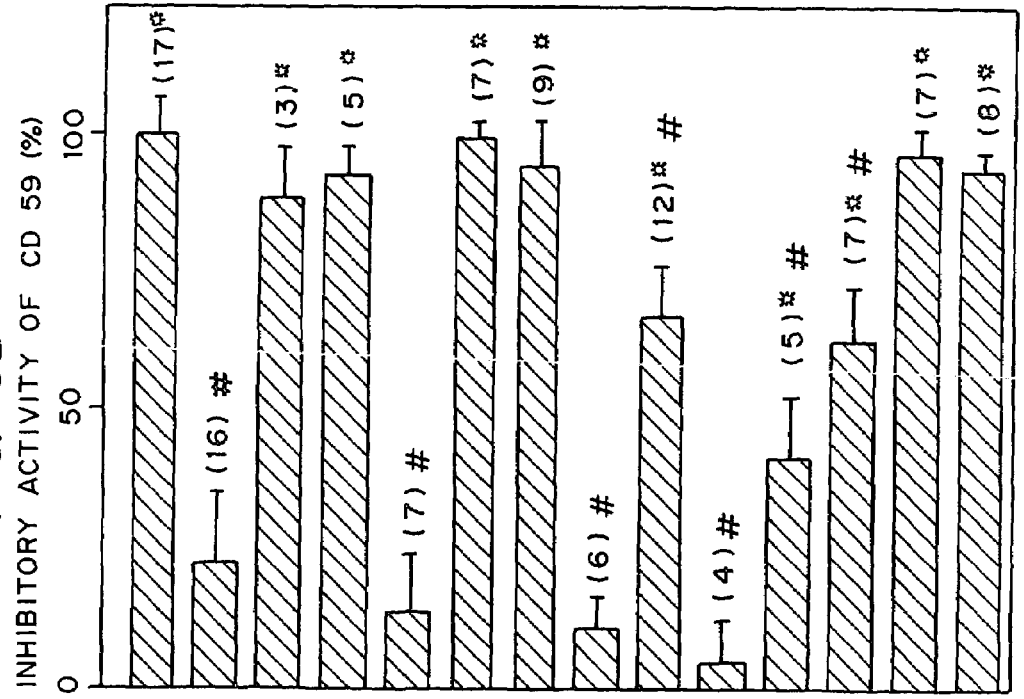
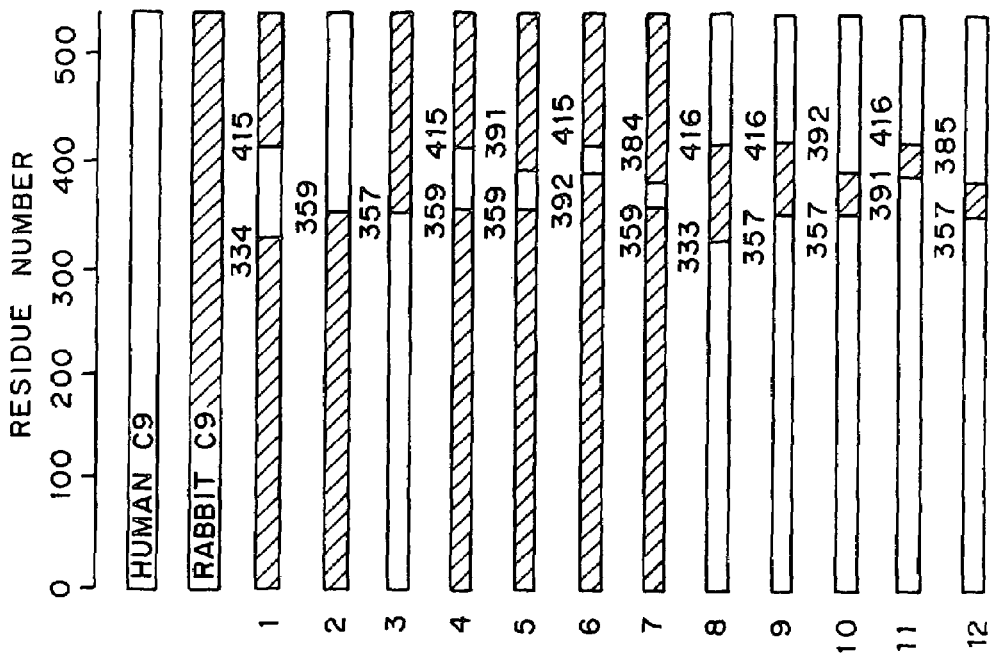
FIG. 9A
FIG. 9B

COMPOSITIONS AND METHODS TO INHIBIT FORMATION OF THE C5B-9 COMPLEX OF COMPLEMENT

The U.S. government has certain rights in this invention by virtue of grant HL36061 from the Heart, Lung and Blood Institute, National Institutes of Health to Peter J. Sims.

The present invention is generally in the area of compounds regulating complement-mediated inflammation, and is specifically directed to compounds interacting with assembly of the C5b-9 complex.

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in the normal serum of man and other vertebrates.

The classic complement pathway involves an initial antibody recognition of, and binding to, an antigenic site (SA) on a target cell. This surface bound antibody subsequently reacts with the first component of complement, C1q, forming a C1-antibody complex with $Ca^{+2}$, C1r, and C1s which is proteolytically active. C1s cleaves C2 and C4 into active components, C2a and C4a. The C4b,2a complex is an active protease called C3 convertase, and acts to cleave C3 into C3a and C3b. C3b forms a complex with C4b,2a to produce C4b,2a,3b, which cleaves C5 into C5a and C5b. C5b combines with C6. The C5b,6 complex combines with C7 to form the ternary complex C5b,6,7. The C5b,6,7 complex binds C8 at the surface of the cell, which may develop functional membrane lesions and undergo slow lysis. Upon binding of C9 to the C8 molecules in the C5b,6,7,8 complex, lysis of bacteria and other foreign cells is rapidly accelerated.

The C5b-9 proteins of the human plasma complement system have been implicated in non-lytic stimulatory responses from certain human vascular and blood cells. The capacity of C5b-9 to modify membrane permeability and to selectively alter ion conductance is thought to elicit these non-lytic responses from human cells. In the case of human blood platelets and vascular endothelium, assembly of the C5b-9 complex initiates a transient and reversible depolarization of the plasma membrane potential, a rise in cytosolic $Ca^{+2}$, metabolic conversion of arachidonate to thromboxane or prostacyclin, and the activation of intracellular protein kinases. In addition, human platelets exposed to C5b-9 undergo shape changes, secretory fusion of intracellular storage granules with plasma membrane, and the vesiculation of membrane components from the cell surface. Human endothelial cells exposed to the human C5b-9 proteins secrete high molecular weight multimers of the platelet adhesion protein, von Willibrand Factor (vWF), and the intracellular granule membrane protein, P-selectin (GMP140), is translocated from the Weibel-Palade body to the endothelial surface. High molecular weight multimers of vWF have been implicated in the pathogenesis of vaso-occlusive platelet adherence to endothelium and cell surface P-selectin (GMP140) has been implicated in the adherence of inflammatory leukocytes to endothelium.

These effects of complement proteins C5b-9 on platelet and endothelial cells alter the normal regulation of the enzymes of the plasma coagulation system at these cell surfaces. For example, the generation of platelet membrane microparticles by vesiculation is accompanied by the exposure of membrane binding sites for coagulation factor Va. Binding of factor Va to the platelet plasma membrane and to these membrane microparticle sites initiates assembly of the prothrombinase enzyme complex. This complex in turn accelerates coagulation factor Xa activation of prothrombin to thrombin which promotes plasma clotting. Similarly, C5b-9 binding to the endothelial cell results in the exposure of plasma membrane receptors for the prothrombinase complex, thereby accelerating the generation of thrombin from prothrombin at the endothelial surface.

This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

Assembly of the C5b-9 complex is normally limited in plasma by the amount of C5b generated by proteolysis of C5 to its biologically-active fragments C5b and C5a. In addition to plasmin and other plasma or cell-derived proteases, two enzymes of the complement system can cleave C5 to C5a and C5b, the membrane-stabilized enzyme complexes C4b2a and C3bBb (C5-convertases). The activity of these two enzymes is normally inhibited on the surface of human blood and vascular membranes by the plasma membrane proteins, "membrane cofactor protein" (CD46), described by Lublin and Atkinson, *Current Topics Microbiol. Immunol.* 153:123 (1989) and "decay-accelerating factor: (CD55), Medof, et al., *J. Exp. Med.* 160:1558 (1984).

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets and b) local intravascular complement activation resulting in membrane deposition of C5b-9 complexes accompanies coronary vessel occlusion and may affect the ultimate extent of myocardial damage associated with infarction.

There is now considerable evidence that the human erythrocyte membrane as well as the plasma membranes of other human blood cells and vascular endothelium are normally protected from these effects of complement by cell-surface proteins that specifically inhibit activation of the C5b-9 pore upon C9 binding to membrane C5b-8, as reported by Holguin, M. H., et al., *J. Clin. Invest.* 84, 7–17 (1989); Sims, P. J., et al., *J. Biol. Chem.* 264, 19228–19235 (1989); Davies, A., et al., *J. Exp. Med.* 170, 637–654 (1989); Rollins, S. A., and Sims, P. J. *J. Immunol.* 144, 3478–3483 (1990); and Hamilton, K. K., et al., *Blood* 76, 2572–2577 (1990). Plasma membrane constituents reported to exhibit this activity include homologous restriction factor (HRF) (C8-binding protein), as described by Zalman, L. S., et al., *Proc. Natl. Acad. Sci., U.S.A.* 83, 6975–6979 (1986) and Schonermark, S., et al., *J. Immunol.* 136, 1772–1776 (1986), and the leukocyte antigen CD59, described by Sugita, Y., et al., *J. Biochem. (Tokyo)* 104, 633–637 (1988); Holguin, M. H., et al., (1989); Sims, P. J., et al., (1989); Davies, A., (1989); Rollins, S. A., and Sims, P. J. (1990); and Hamilton, K. K., et al., (1990).

Accumulated evidence suggest that these two proteins exhibit quite similar properties, including the following: both HRF and CD59 are tethered to the cell surface by a glycolipid anchor, and are deleted from the membranes of the most hemolytically sensitive erythrocytes that arise in the stem cell disorder paroxysmal nocturnal hemoglobinuria; the activity of both inhibitors is species-restricted, showing selectivity for C8 and C9 that are derived from homologous (i.e. human) serum; and both HRF and CD59 appear to function by inhibiting the activation of C9, decreasing the incorporation of C9 into the membrane C5b-9 complex, and limiting propagation of the C9 homopolymer. Whereas the molecular identity of CD59 is now well-established, no peptide or cDNA sequence has yet been reported for HRF and its molecular identity remains unresolved (Sugita, Y., et al., *J. Biochem.* (*Tokyo*) 104, 633–637 (1988); Holguin, M. H., et al., (1989); Sims, P. J., et al., (1989); Davies, A. (1989); Rollins, S. A., and Sims, P. J. (1990)).

Human (hu) CD59 antigen is a 18–21 kDa plasma membrane protein that functions as an inhibitor of the C5b-9 membrane attack complex (MAC) of human complement. CD59 interacts with both the C8 and C9 components of MAC during its assembly at the cell surface, thereby inhibiting formation of the membrane-inserted C9 homopolymer responsible for MAC cytolytic activity. This serves to protect human blood and vascular cells from injury arising through activation of complement in plasma, as described in U.S. Pat. No. 5,136,916 to Sims and Wiedmer. CD59's inhibitory activity is dependent upon the species of origin of C8 and C9, with greatest inhibitory activity observed when C9 is from human or other primates. By contrast, CD59 exerts little or no inhibitory activity towards C8 or C9 of most other species, including rabbit (rb). Because the activity of CD59 is largely restricted to regulating hu C9, and the activity of analogous complement inhibitors expressed by cells of other species is likewise generally selective for homologous C9, xenotypic cells and tissue are particularly susceptible to complement-mediated destruction due to unregulated activity of MAC. This phenomenon underlies hyperacute immune rejection after xenotransplantation.

Analysis of the physical association of CD59 with components of MAC suggested that separate binding sites for CD59 are contained within the α-chain of hu C8 and within hu C9. The complement-inhibitory activity of CD59 is species-selective, and is most effective towards C9 derived from human or other primate plasma. The species-selective activity of CD59 was used to map the segment of human C9 that is recognized by this MAC inhibitor, using recombinant rabbit/human C9 chimeras that retain lytic function within the MAC (Husler, T, Lockert D H, Kaufman K M, Sodetz J M, Sims P J (1995) *J. Biol. Chem.* 270:3483–3486). These experiments indicated that the CD59 recognition domain was contained between residues 334–415 in human C9, as described in PCT/US96/17940 "C9 Complement Inhibitor" by Oklahoma Medical Research Foundation.

It is apparent that additional or alternative inhibitors of the assembly of the C5b-9 complex would be advantageous in modulation of complement-mediated inflammation. It is also clear that inhibitors which are extremely specific and which are directed to the most critical regions involved in assembly or function of the complex would be most effective as inhibitors of complement-mediated inflammation, with the least likelihood of non-specific side effects.

It is therefore an object of the present invention to provide a method and materials for specifically modulating complement-mediated inflammation mediated by CD59 binding to C9.

SUMMARY OF THE INVENTION

Compounds modulating CD59 mediated complement activity, compositions including these compounds, and methods of making and using the compounds are disclosed, which are based on the identification of the hu CD59 amino acid residues which serve as the binding site for CD59-C9 interactions. These residues correspond to amino acid residues 42–58, and bind to the region of C9 corresponding to human 334–418, more specifically, between amino acid residues 359 and 384. Compounds can be derived using the basic amino acid sequence and corresponding three dimensional structure within the protein using any of several techniques known to those skilled in the art, including rational drug design using computer databases and modeling of peptide/protein-ligand binding, antibodies and anti-idiotypic antibodies generated to the proteins or peptides containing this peptide sequence, and modified peptides. Those compounds imitating the structure and/or function of the peptide region are referred to herein as "peptidomimetics", and include small molecules which present the surface exposed side chains in these amino acids in the same relative positions, compounds identified by combinatorial chemistry techniques which bind to active portions of human C9, as well as modified peptides. In particular, peptidomimetics and peptides of less than 40 amino acid residues and having the structure and function of human CD59 amino acid residues 42–58 of SEQ ID NO:3 are contemplated, the peptidomimetic or peptide binding specifically to human C9 at amino acid residues 26–51 of SEQ ID NO:14, as well as methods of their use for inhibiting human C5b-9 complex assembly.

The compounds can be used to inhibit complement by binding to C9 analogously to CD59, or to maintain complement inhibition, by blocking CD59 binding to C9. The compounds can be administered locally or systemically in any suitable carrier in an amount effective to either inhibit complement or block the inhibition of complement, in a patient in need of treatment thereof.

BRIEF DESCRIPTION OF THE DRAWINGS

FIG. 1A shows the alignment of the amino acid sequences of human (hu) and rabbit (rb) CD59 (Sequence ID No. 1 and Sequence ID No. 2, respectively).

FIGS. 2A, 2B, and 2C are schematics showing the chimeric hu/rb CD59 constructs (FIG. 2A), and graphs of cytolysis (percent release of BCECF Dye versus CD59 per cell (arbitrary fluorescence units) for the human/rabbit chimeras assayed using hu C8/C9 (FIG. 2B) or rb C8/C9 (FIG. 2C).

FIGS. 3A, 3B, and 3C are schematics showing the chimeric hu/rb CD59 constructs (FIG. 3A), and graphs of cytolysis (percent release of BCECF Dye versus CD59 per cell (arbitrary fluorescence units) for the human/rabbit chimeras assayed using hu C8/C9 (FIG. 3B) or rb C8/C9 (FIG. 3C).

FIGS. 4A, 4B, and 4C are schematics showing the chimeric hu/rb CD59 constructs (FIG. 4A), and graphs of cytolysis (percent release of BCECF Dye versus CD59 per cell (arbitrary fluorescence units) for the human/rabbit chimeras assayed using hu C8/C9 (FIG. 4B) or rb C8/C9 (FIG. 4C).

FIGS. 5A, 5B, and 5C are schematics showing the chimeric hu/rb CD59 constructs (FIG. 5A), and graphs of cytolysis (percent release of BCECF Dye versus CD59 per cell (arbitrary fluorescence units) for the human/rabbit chimeras assayed using hu C8/C9 (FIG. 5B) or rb C8/C9 (FIG. 5C).

FIGS. 6A, 6B, and 6C are schematics showing the chimeric hu/rb CD59 constructs (FIG. 6A), and graphs of cytolysis (percent release of BCECF Dye versus CD59 per cell (arbitrary fluorescence units) for the human/rabbit chimeras assayed using hu C8/C9 (FIG. 6B) or rb C8/C9 (FIG. 6C).

FIGS. 8A–B is a sequence alignment of the amino acid sequences for CD59 of human, baboon, African green monkey, owl monkey, marmoset, HVS-15, pig, sheep, rabbit, rat, and mouse origin. Human is Sequence ID No. 3, baboon is Sequence ID No. 4, African green monkey (Afr grn mnky) is Sequence ID No. 5, owl monkey is Sequence ID No. 6, marmoset is Sequence ID No. 7, HVS-15 is Sequence ID No. 8, pig is Sequence ID No. 9, sheep is Sequence ID No. 10, rabbit is Sequence ID No. 11, rat is Sequence ID No. 12, and mouse is Sequence ID No. 13.

FIGS. 9A and 9B are schematics of hu/rb C9 chimeric constructs (FIG. 9A) and a plot of the inhibitory activity of the chimeric C9 constructs (FIG. 9B). Bar graph (right panel) summarizes combined results of all experiments measuring the inhibitory activity of CD59 with the recombinant human/rabbit chimeras of C9. In each assay, hemolytic titrations of C9 were performed against C5b-8 chE in the presence and absence of membrane CD59 and the percent reduction of hemolysis due to CD59 (ordinate) was determined, with normalization to that observed for hu C9 (100% inhibition). Error bars denote mean+S.D., parentheses indicate number of independent experiments; asterisks (*) indicate significance (p<0.01) when compared to rb C9; pound signs (#) indicate significance (p<0.01) when compared to hu C9. To the left of each data bar, the protein assayed is depicted so as to designate those portions of the polypeptide containing hu C9 (open) or rb C9 (shaded) sequence. Numbers above each construct indicate the junctional hu C9 residue at each transition between human and rabbit protein sequence. Bars designated as human C9 and rabbit C9 denote recombinantly-expressed hu and rb C9, respectively. Recombinant C9 chimeras (designated #1–12) contain human (H) or rabbit (R) sequence according to the deduced mature primary structure of hu and rb C9. In some C9 chimeras, the numbering appears discontinuous because of gaps in the alignment of the human and rabbit sequences: 1, R1-338H334–415R425–536; 2, R1-363H359–538; 3, H1-357R363–536; 4, R1-363H359–415R425–536; 5, R1-363H359–391R401–536; 6, R1-400H392–415R425–536; 7, R1-363H359–384R394–536; 8, H1-333R339–424H416–538; 9, H1-357R363–424H416–538; 10, H1-357R363–400H392–538; 11, H1-391R401–424H416–538; 12, H1-357R363–393H385–538.

DETAILED DESCRIPTION OF THE INVENTION

Figure 1B:
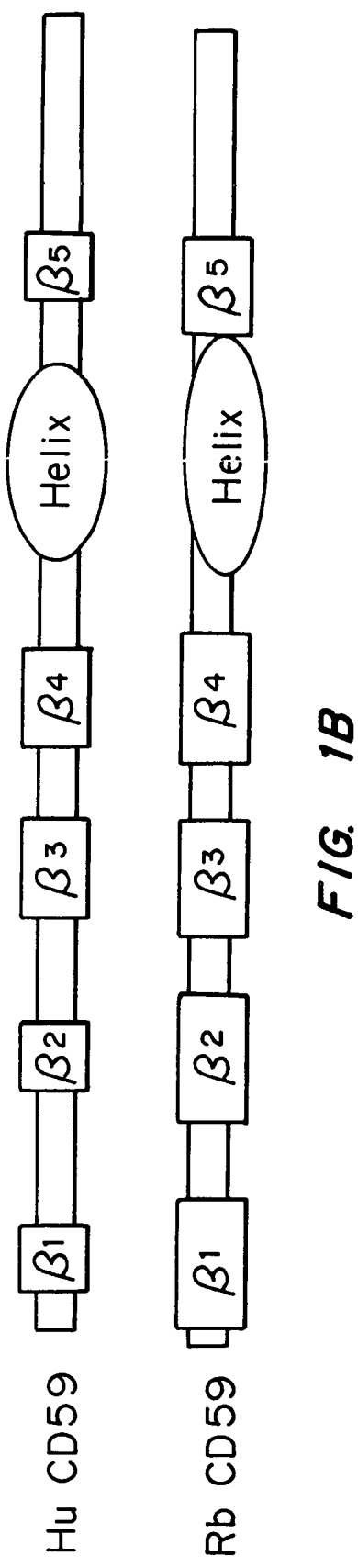
FIG. 1B shows the alignment of the domains of hu and rb CD59.

Compounds modulating CD59 mediated complement activity, compositions including these compounds, and methods of making and using the compounds are disclosed, which are based on the identification of the hu CD59 amino acid residues which serve as the binding site for CD59-C9 interactions. These residues correspond to amino acid residues 42–58 (amino acids 42 to 58 of SEQ ID NO:3), and bind to the region of C9 corresponding to human 334–418, more specifically, between amino acid residues 359 and 384. Compounds can be derived using this basic amino acid sequence and corresponding three dimensional structure within the protein using any of several techniques known to those skilled in the art, including rational drug design using computer data bases and modeling of peptide/protein-ligand binding, antibodies and anti-idiotypic antibodies generated to the proteins or peptides containing this peptide sequence, and modified peptides. Those compounds imitating the structure and/or function of the peptide region are referred to herein as "peptidomimetics", and include small molecules which present the surface exposed side chains in these amino acids in the same relative positions, compounds identified by combinatorial chemistry techniques which bind to the active portions of human C9, as well as modified peptides.

As described in PCT/US96/17940 "C9 Complement Inhibitor" by Oklahoma Medical Research Foundation, hu CD59 interacts with a segment of human C9 (hu C9) between residues 334–415, immediately C-terminal to the predicted membrane-inserting domain of C9. This segment of C9 contains a region of markedly divergent sequence when hu C9 is compared to C9 of other species, with greatest divergence noted for the peptide segment contained within an internal Cys359–Cys384 disulfide in hu C9.

Human CD59 shows negligible complement inhibitory activity toward rabbit C5b-9, and rabbit CD 59 shows negligible complement inhibitory activity toward human C5b-9. Rabbit and human C5b-9 proteins work interchangeably and can assemble into functional lytic C5b-9 complexes. Recombinant DNA techniques, described in more detail in the Examples, were used to prepare various chimeric rabbit/human proteins to map the specific peptide residues involved in the binding interaction between CD59 and the C8 and C9 components of the C5b-9 complex to determine the sequence contained in CD59 which affords species specificity. It has been discovered that the entire species selective recognition of hu CD59 is encoded by amino acid residues 42–58 of human CD59. Although described herein with reference to the amino acid residues of the human proteins, it is understood that there are corresponding regions in other molecules of different origin, and that one skilled in the art would modify molecules of a different species of origin for use in that species in the same manner as described herein with reference to human CD59 and hu C9.

Unless otherwise noted, all references to amino acid positions in CD59 refer to the numbering of amino acids where the first amino acid in mature CD59 is amino acid number 1. Thus, amino acids 42–58 of CD59 refers to the forty-second through fifty-eighth amino acids of mature CD59. This numbering is used in FIGS. 1A and 8 and SEQ ID NO:3. SEQ ID NO:1 includes the signal peptide sequence. Rabbit CD59 contains an additional Ser residue before the highly-conserved N-terminal $Leu^1$ found in all other CD59 homologues that have been sequenced to date. Therefore, in order to simplify discussion of the aligned residues of hu and rb CD59 in various chimeric constructs, residues of the mature rb CD59 polypeptide have been renumbered herein commencing with [N-$Ser^0$]-$Leu^1$-$Met^2$-$Cys^3$- etc. FIG. 1). All references to amino acids in rb C59 are based on this re-numbering of residues in the mature polypeptide.

The active surface exposed side chains that are available to bind C8/C9 were identified from the solution structure of hu CD59, as determined from published NMR data and the knowledge of the active portion of the CD59 molecule. These side chains are the side chains of histidine at position 44, asparagine at position 48, aspartic acid at position 49, threonine at positions 51 and 52, arginine at position 55 and glutamic acid at position 58. Compounds which present the side chains at the same relative positions will behave in a manner similar to hu CD59. NMR structures for CD59 are described in deposits by Kieffer et al., Human Complement Regulatory Protein CD59 (Extracellular Region, Residues 1–70) (NMR, 10 Structures), MMDB Id: 891, PDB Id: 1ERH; Kieffer et al., Human Complement Regulatory Protein CD59 (Extracellular Region, Residues 1–70) (NMR, Restrained), MMDB Id: 890, PDB Id: 1ERG; Fletcher et al., CD59 Complexed With Glcnac-Beta-1,4-(Fuc-Alpha-1,6)-Glcnac-Beta-1 (Nmr, 10 Structures), MMDB Id: 498, PDB Id: 1CDS; Fletcher et al., CD59 Complexed With Glcnac-Beta-1,4-Glcnac-Beta-1 (Nmr, 10 Structures), MMDB Id: 497, PDB Id: 1CDR. The 1CDS and 1CDR deposits by Fletcher et al. are preferred.

Compounds which bind to the active portion of the hu C9 can inhibit complement activity by performing substantially the same role as hu CD59. Compounds which bind to the active portion of hu CD59 can block the ability of CD59 to inhibit complement activity.

Compounds Useful as Mimics of hu CD59 and C9

A. Hu CD59 and C9 Chimeras

As described in the examples, chimeric proteins have been made which substitute the critical amino acid residues for binding activity in C9 or CD59 of one species, typically human, into a protein of a different species. The examples demonstrate how these chimeric proteins are useful to conduct studies of function and structure, as well as to generate antibodies to the critical regions, as described below. The compounds an also be used, for example, for competitive binding assays, combinatorial chemistry to isolate compounds which only bind to the active portion of hu CD59, and as therapeutics, although their therapeutic uses may be limited to non-human animals.

B. Antibodies to amino acid residues 42–58 of hu CD59 and amino acid residues 359–384 of hu C9.

Antibodies immunoreactive with the hu CD59 peptide (amino acid residues 42–58), the hu C9 peptide (amino acid residues 359–384), or an anti-idiotypic antibody to these antibodies immunoreactive with the CD59 or C9 peptides can be prepared using the techniques described herein.

1. In vivo Immunization of Animals

Animals such as mice may be immunized by administration of an amount of immunogen such as the CD59 peptide, an antibody to the CD59 peptide, the C9 peptide or an antibody to the C9 peptide, effective to produce an immune response. Preferably a mouse is subcutaneously injected in the back with 100 micrograms of antigen, followed three weeks later with an intraperitoneal injection of 100 micrograms of immunogen with adjuvant, most preferably Freund's complete adjuvant. Additional intraperitoneal injections every two weeks with adjuvant, preferably Freund's incomplete adjuvant, may be necessary until the proper titer in the mouse's blood is achieved. In order to use the mice for fusion and hybridoma production, a titer of at least 1:5000 is preferred, and a titer of 1:100,000 or more is most preferred.

In a preferred embodiment, the antibodies are raised by standard immunization of rabbits with chimeric rabbit/human CD59 protein in which human CD59 residues 42–58 replace the corresponding residues in the rabbit CD59 polypeptide or chimeric rabbit/human C9 protein in which human C9 residues 359–384 replace the corresponding residues in the rabbit C9 polypeptide, based upon alignment of the human and rabbit protein sequences. In another embodiment, these antibodies are raised by standard immunization of mice with chimeric mouse/human CD59 protein in which human CD59 residues 42–58 replace the corresponding residues in the mouse CD59 polypeptide, based upon alignment of the human and mouse protein sequences. The antibodies can then be purified, for example, by affinity purification on columns containing human CD59.

2. In vitro Immunization

The technique of in vitro immunization of human lymphocytes is frequently employed to generate a large variety of human monoclonal antibodies. Techniques for in vitro immunization of human lymphocytes are well known to those skilled in the art. See, e.g., T. Inai, et al., *Histochemistry* (Germany), 99(5):335–362 (May 1993); A. Mulder, et al., *Hum. Immunol.*, 36(3):186–192 (March 1993); H. Harada, et al., *J. Oral Pathol. Med.* (Denmark), 22(4): 145–152 (April 1993); N. Stauber, et al., *J. Immunol. Methods* (Netherlands), 161(2):157–168 (May 26, 1993); and S. Venkateswaran, et al., *Hybridoma*, 11(6) 729–739 (December 1992). These techniques can be used to produce antigen-reactive human monoclonal antibodies, including antigen-specific IgG, and IgM human monoclonal antibodies.

3. Humanization of Antibodies

Since the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a less xenografic rejection stimulus when introduced to a human recipient.

To accomplish humanization of a selected mouse monoclonal antibody, the CDR grafting method described by Daugherty, et al., *Nucl. Acids Res.*, 19:2471–2476 (1991) may be used. Briefly, the variable region DNA of a selected animal recombinant anti-idiotypic ScFv is sequenced by the method of Clackson, T., et al., *Nature*, 352:624–688, 1991. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

4. Use of Chimeras to Select Particularly Active Antibodies

Antibodies which bind to inactive portions of the peptides will be less effective than antibodies which bind to the active portions. One can use the chimeric peptides described above to select particularly preferred antibodies.

For example, once an antibody is prepared, it can be bound to the appropriate peptide (hu CD59 or C9), and chimeras containing the active portion of the peptide from the rabbit sequence and the remainder of the peptide containing the human sequence can be used in a competitive binding study. If the chimera is effective at competitively binding with the antibody, the antibody is likely binding to an inactive portion of the peptide. A chimera containing the active portion of the peptide from the human sequence and the inactive portion of the peptide from the rabbit sequence can also be used in a competitive binding study. If the chimera is effective at competitively binding with the antibody, the antibody is likely bound to the active portion of the peptide.

C. Compounds Identified by Combinatorial Chemistry

Molecules with a given function, catalytic or ligand-binding, can be selected for from a complex mixture of random molecules in what has been referred to as "in vitro genetics" (Szostak, *TIBS* 19:89, 1992) or combinatorial chemistry. One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Using methodology well known to those of skill in the art, in combination with various combinatorial libraries, one can isolate and characterize those compounds which bind to or interact with the desired target. The relative binding affinity of these compounds can be compared and optimum compounds identified using competitive binding studies which are well known to those of skill in the art.

Identification of compounds which bind the active portion of the hu CD59 and hu C9 can be simplified using the data regarding the active portions of these molecules identified using chimeric molecules. For example, the human CD59 or C9 can be bound to a solid support, and interacted with various combinatorial libraries. Those molecules which do not bind these molecules at all are removed immediately by elution with a suitable solvent. Those molecules which bind to inactive portions of the CD59 or C9 molecules can be removed by competitive binding with an excess of a chimeric peptide with the inactive portions represented by human sequences and the active portion represented by the rabbit sequence. Those compounds which bind to the active portion of the CD59 or C9 will remain bound to the solid support, whereas compounds bound to inactive portions of these molecules will be removed from the column. Finally, those compounds still bound to the column (which are bound to the active portions of these molecules) can be removed, for example, by competitive binding with CD59 or C9, or chimeras including only the active human portion of these molecules. Following removal, these compounds can be identified and their relative binding affinity compared as described above.

D. Rational Drug Design

Drugs with the ability to mimic the function of the hu CD59 and C9 can be identified using rational drug design. The compounds preferably include the surface active functional groups of hu CD59 or C9, or substantially similar groups, in the same or substantially similar orientation, so that the compounds possess the same or similar biological activity. The surface active functional groups in CD59 and C9 possess a certain orientation when they are in their active conformations, in part due to their secondary or tertiary structure. Rational drug design involves both the identification and chemical modification of suitable compounds which mimic the function of the parent molecules.

Compounds that mimic the conformation and desirable features of a particular peptide, e.g., an oligopeptide, but that avoid undesirable features, e.g., flexibility (loss of conformation) and metabolic degradation, are known as "peptidomimetics". Peptidomimetics that have physical conformations which mimic the three dimensional structure of amino acids 42–58, in particular, which have surface active groups as described herein, are active in inhibiting the formation of the C5b-9 complex. Peptidomimetics that have physical conformations which mimic the three dimensional structure of amino acids 359–384 of hu C9 are active in blocking complement inhibition.

The physical conformation of hu CD59 and C9 are determined, in part, by their primary, secondary and tertiary structure. The primary structure of a peptide is defined by the number and precise sequence of amino acids in CD59 or C9. The secondary structure is defined by the extent to which the polypeptide chains possess any helical or other stable structure. The tertiary structure is defined by the tendency for the polypeptides to undergo extensive coiling or folding to produce a complex, somewhat rigid three-dimensional structure.

1. Computer Modeling Software

Computer modeling technology allows visualization of the three-dimensional atomic structure of a selected molecule and the rational design of new compounds which will mimic the molecule or which will interact with the molecule. The three-dimensional structure can be determined based on data from x-ray crystallographic analyses and/or NMR imaging of the selected molecule, or from ab initio techniques based solely or in part on the primary structure, as described, for example, in U.S. Pat. No. 5,612,895 to Balaji et al. The computer graphics systems enable one to predict how a new compound will link to the target molecule and allow experimental manipulation of the structures of the compound and target molecule to perfect binding specificity.

Many databases and computer software programs are known that can be used to design drugs. For example, see Ghoshal et al., "Computer Aids in Drug Design—Highlights" (1996) *Pol. J. Pharmacol.* 48(4), 359–377; Wendoloski et al., "Biophysical Tools for Structure-Based Drug Design" (1993) *Pharmacol. Ther.* 60(2), 169–183; Lybrand, "Ligand-Protein Docking and Rational Drug Design" (1995) *Curr. Opin. Struct. Biol.* 5(2), 224–228; Kleinberg and Wanke, "New Approaches and Technologies in Drug Design and Discovery" (1995) *Am. J. Health Syst. Pharm.* 52(12), 1323–1336; Kubinyi, "Strategies and Recent Technologies in Drug Discovery" (1995) *Pharmazie* 50(10), 647–662; Archakov et al., (1996) *Vestn. Ross. Akad. Med. Nauk.* 1, 60–63; Taylor and Smith, "The Word Wide Web as a Graphical User Interface to Program Macros for Molecular Graphics, Molecular Modeling, and Structure-Based Drug Design" (1996) *J. Mol. Graph.* 14(5), 291–296; Huang et al., "Development of a Common 3D Pharmacophore for Delta-Opioid Recognition From Peptides and Non-Peptides Using a Novel Computer Program" (1997) *J. Comput. Aided Mol. Des.* 11(1), 21–78; and Li et al., "A computer Screening Approach to Immunoglobulin Superfamily Structures and Interactions: Discovery of Small Non-Peptidic CD4 Inhibitors and Novel Immunotherapeutics (1997) *Proc. Natl. Acad. Sci. USA* 94(1), 73–78.

Data bases including constrained metabolically stable non-peptide moieties may be used to search for and to suggest suitable CD59 or C9 analogs. Searches can be performed using a three dimensional data base for non-peptide (organic) structures (e.g., non-peptide analogs, and/or dipeptide analogs) having three dimensional similarity to the known structure of the active regions of these molecules. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331–2339 (1979). Alternatively, three dimensional structures generated by other means such as molecular mechanics can be consulted. See., e.g., Burkert, et al., *Molecular Mechanics*, American Chemical Society, Washington, D.C. (1982); and Weiner, et al., *J. Am. Chem. Soc.*, 106(3): 765–84 (Eng.) (1984).

Search algorithms for three dimensional data base comparisons are available in the literature. See, e.g., Cooper, et al., *J. Comput.-Aided Mol. Design*, 3: 253–259 (1989) and references cited therein; Brent, et al., *J. Comput.-Aided Mol. Design*, 2: 311–310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the CD59/C9 interactions.

2. Structural Data to be Used with the Modeling Software

The chimeric studies described herein have determined which amino acids are present in the active binding region in both hu CD59 and C9. With respect to CD59, the active surface exposed side chains that are available to bind C8/C9 were identified from the solution structure of hu CD59, as determined from published NMR data and the knowledge of the active portion of the CD59 molecule. These side chains are the side chains of histidine at position 44, asparagine at position 48, aspartic acid at position 49, threonine at positions 51 and 52, arginine at position 55 and glutamic acid at position 58. Accordingly, the receptor geometry and active conformation of the active region in hu CD59 is known, by virtue of existing NMR (Nuclear Magnetic Resonance) data. Using the information regarding bond angles and spatial geometry of the critical amino acids, one can use computer programs as described herein to develop peptidomimetics.

Chemically modified analogs of the active portion of hu C9 can also be identified using the techniques described above.

3. Chemical Modifications

Peptidomimetics can be modified to increase bioavailability. Preferably, the compounds are structurally constrained such that the surface active groups are oriented in the active conformation. The compounds can further include chemical modifications that minimize the metabolic degradation of the compounds once they are administered. See, for example, Spatola, A. F. *Chemistry and Biochemistry of Amino Acids, Peptides, and Proteins* (Weistein, B, Ed.), Vol. 7, pp. 257–357, Marcel Dekker, New York (1983), which describes the use of the methylenethio bioisostere [$CH_2S$] as an amide replacement; and Szelke et al., *In Peptides: Structure and Function, Proceedings of the Eighth American Peptide Symposium*, (Hruby and Rich, Eds.); pp. 579–582, Pierce Chemical Co., Rockford, Ill. (1983), which describes methyleneamino [$CH_2NH$] and hydroxyethylene [$CHOHCH_2$] bioisosteres.

CD59 and C9 have flexible and rigid portions. The flexible portions of the structure can be replaced with suitable bioisosteres or equivalents, so that the active conformation can be maintained. As defined herein, the term "bioisostere" refers to atoms or groups of atoms which are of similar size to the atom or group of atoms which are to be replaced, wherein the compound containing the replacement atom or group of atoms retains, to a substantial degree, the biological activity of the original, unmodified peptide. See, for example, Nelson, Mautner, and Kuntz, at pp. 227, 271 and 285, respectively, in *Burger's Medicinal Chemistry*, Part 1, the Basis of Medicinal Chemistry, 4th Edition, M. E. Wolff, ed. (John Wiley & Sons, NY, 1980).

Numerous peptide backbone substitutions are known to those of skill in the art which can provide peptidomimetics with improved physical and chemical properties, including enhanced rigidity and chemical and/or metabolic stability. Suitable substitutions include modifying one or more of the amide bonds by replacing the amide nitrogen with an oxygen atom, or a sulfur atom, or by replacing H at the amide nitrogen with an alkyl, aryl, aralkyl or alkaryl group, producing an N-substituted amide, or by replacing the amide group with a methylene moiety, optionally substituted with one or two alkyl, aryl, aralkyl or alkaryl groups, which can in turn optionally be substituted with various functional groups, such as halogens, carbonyl groups, amines, nitriles, azides, thiols, hydroxy groups, and carboxylic acid groups. The alkyl groups are preferably $C_{1-6}$ straight, branched or cyclic groups. Further, one or more of the amide bonds present in the peptide backbone can be modified, for example, by replacing the amide carbonyl group with a methylene group (optionally substituted as described above), a thiocarbonyl group, a sulfone moiety or a sulfoxide moiety.

The peptide can be further modified by introducing alkyl, aryl, aralkyl or alkaryl substituents, optionally substituted as described above, at one or more of the alpha-carbon atoms, such that the peptide backbone is unchanged, but additional side chain substituents are present in the chemically modified analog. Suitable α-carbon atom modifications include cyclopropyl groups, ethylidene groups, and primary, secondary or tertiary amines.

Each of these modifications can be introduced into the peptide chain in either orientation (i.e., in the orientation shown, or in the "reverse" orientation). In addition, various substituents on the amide nitrogen and the α-carbon can be bound to one another, thereby forming a cyclic structure which is a relatively constrained analog. Other constrained, cyclic structures can also be prepared by linking various substituents to form cyclic structures using chemical techniques know to those of skill in the art. Other modifications include those described in U.S. Pat. No. 5,612,895 to Balaji et al., the contents of which are hereby incorporated by reference.

Chemically modified analogs are typically more resistant to enzymatic cleavage than the native peptides from which they are derived because the modified residues are not typically recognized by the enzymes which degrade naturally occurring proteins. Further, the backbone and side chains of peptides can be modified to provide peptidomimetics with reduced conformational flexibility. Accordingly, the possibility that the peptide will adopt conformation(s) other than the specifically desired conformation(s) can be substantially minimized by appropriate modification.

Methods of Preparing the Compounds

Once the desired analog (including backbone and side chain modifications, as appropriate) has been identified, chemical synthesis is undertaken, employing standard synthetic techniques. For a given target compound, the skilled artisan can readily identify suitable synthetic approaches for the preparation of the target compound. Particular techniques for synthesizing certain classes of compounds are described in more detail below.

1. Methods of Preparing Nucleotide Molecules

Nucleotide molecules which bind amino acids 42–58 of hu CD59 can be generated in vitro, and then inserted into cells. Oligonucleotides can be synthesized on an automated synthesizer (e.g., Model 8700 automated synthesizer of Milligen-Biosearch, Burlington, Mass. or ABI Model 380B). (see, e.g., Offensperger et al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications).

To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., 1992). Other nucleoside modifications that reduce susceptibility to intracellular degradation are well known to those of skill in the art, and are intended to be within the scope of the compositions and methods described herein.

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620 (1980) (phosphotriester method).

2. Preparation of Peptides

Proteins can be expressed recombinantly or naturally and cleaved by enzymatic digest, expressed from a sequence encoding just a peptide, or synthesized using standard techniques. It is a routine matter to make appropriate peptides, test for binding, and then utilize the peptides. The peptides are easily prepared by standard techniques. They can also be modified to increase in vivo half-life, by chemical modification of the amino acids or by attachment to a carrier molecule or inert substrate, as discussed above. The peptides can also be conjugated to a carrier protein by its N-terminal cysteine by standard procedures such as the commercial Imject kit from Pierce Chemicals or expressed as a fusion protein, which may have increased stability. Solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891, the contents of which are hereby incorporated by reference. These methods can be used to synthesize peptides having identical sequence to the receptor proteins described herein, or substitutions or additions of amino acids, which can be screened for activity as described above.

The peptide can also be prepared as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Methods for Evaluating the Compounds for Biological Activity

After the compounds are synthesized, their biological activity can be evaluated, for example, using competitive binding studies, and iterative refinement of the peptidomimetic (in the case of a constrained analog itself) an then be carried out. Those chemically modified analogs which are biologically active can be employed as peptidomimetics without further modification.

Compositions Including the Compounds

The compounds described above are preferably administered in a pharmaceutically acceptable vehicle. Suitable pharmaceutical vehicles are known to those skilled in the art. For parenteral administration, the compound will usually be dissolved or suspended in sterile water or saline. The compounds can also be administered locally by topical application of a solution, cream, gel, or polymeric material (for example, a Pluronic™, BASF). Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214, the contents of which are hereby incorporated by reference.

Methods of Treatment

An effective amount of the compositions described above is that which achieves the desired effect: either to inhibit assembly of the C5b-9 complex by binding to C9 or to bind to the endogenous CD59 to prevent the CD59 from inhibiting assembly of the C5b-9 complex, thereby increasing complement-mediated activation, injury or cytolysis of cells.

The peptides are generally active when administered parenterally in amounts above about 1 µg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered. Based on studies with other peptide fragments blocking binding, the $IC_{50}$, the dose of peptide required to inhibit binding by 50%, ranges from about 50 µM to about 300 µM, depending on the peptides. These ranges are well within the effective concentrations for the in vivo administration of peptides, based on comparison with the RGD-containing peptides, described, for example, in U.S. Pat. No. 4,792,525 to Ruoshalaghti, et al., used in vivo to alter cell attachment and phagocytosis.

Inhibition of C5b-9 complex assembly is useful for all disorders characterized by excessive complement activation or complement-mediated cytolysis, including, for example, immune disorders and diseases such as immunovasculitis, rheumatoid arthritis, scleroderma, disseminated intravascular coagulation, lupus, paroxysmal nocturnal hemoglobinuria, thrombotic thrombolytic purpura, vascular occlusion, reocclusion after surgery, coronary thrombosis, and myocardial infarction. Inhibition of CD59 is useful as an adjuvant for tumor therapy and as a contraceptive since its been demonstrated that CD59 protects sperm from rejection by antibody and complement in the female genital tract and that CD59 expressed on human tumor cells protect these cells from complement-mediated lysis.

Recent evidence suggests that complement inhibitors specifically directed against hu MAC have potential clinical use in preventing hyperacute rejection of transplanted organs and in reducing the pathological consequences of complement activation in various immune and inflammatory diseases. Identification of the specific protein motif that is responsible for the selective inhibitory action of CD59 towards the pore-forming and cytolytic properties of hu MAC allows one to rationally design small molecules that can mimic the protective effect of this natural cell-surface complement inhibitor.

The present invention will be further understood by reference to the following studies.

EXAMPLE 1

Demonstration of Role of Amino Acids 42–58 Within hu CD59 in the Species-Selectivity of CD59

Experimental Procedures

Materials—Rabbit whole blood and chicken whole blood in ACD were from Cocalico Biologics, Inc. (Reamstown, Pa.). Human serum, rabbit serum, human serum depleted of complemented protein C8 (C8D), human complement proteins (C5b7, C8 and C9) and rabbit complement proteins C8 and C9 were purified and assayed as described previously (Hüsler, T., Lockert, D. H., Kaufman, K. M., Sodetz, J. M., and Sims, P. J. (1995) J. Biol. Chem. 270, 3483–3486; Rollins, S. A. and Sims, P. J. (1990) J. Immunol. 144, 3478–3483; Wiedmer, T. and Sims, P. J. (1985) J. Membr. Biol. 84, 249–25827; and Wiedmer, T. and Sims, P. J. (1985) J. Biol. Chem. 260, 8014–8019). 3-[(3-cholamidopropyl)-dimethylammonio]-1-propane-sulphonate (CHAPS), Phenyl methyl sulfonyl fluoride (PMSF), Dimethyl sulfoxide (DMSO) and bovine serum albumin (BSA) were from Sigma (St. Louis, Mo.). NONIDET™ P-40, and TRITON™ X-100 were from CalBiochem., Inc. (La Jolla, Calif.). Polyoxyethylene 20-soritan monolaurate (Tween 20) was from Fisher Chemical (Fairlawn, N.J.). TA cloning kit, mRNA purification kit, Escherichia coli (E. coli) strain TOP10 and pcDNA3 vectors were obtained from Invitrogen (San Diego, Calif.). All restriction endonucleases were from New England Biolab (Beverly, Mass.). T4 ligase, Hank's balanced salt solution (HBSS), Dulbecco's modified eagle's medium (DMEM) and DNA primers were purchased or synthesized in GIBCO BRL life Technologies (Gaithersburg, Md.). WIZARD™ DNA purification kit was from Promega (Madison, Wis.). Advanced KLENTAQ™ enzymes, cDNA library construction kit, MARATHON racing kit was from Clontech (Palo Alto, Calif.). SEQUENASE™ version 2.0 kit was from Amersham/USB (Cleveland, Ohio). SV-T2 cell line (ATCC163.7) was obtained from American Type Culture Collection (Rockville, Md.). BCECF-AM dye was purchased from Molecular Probes (Eugene, Oreg.). Fetal bovine serum (FBS), calf serum, cell dissociation buffer, L-glutamate, penicillin, streptomycin, trypsin and geneticin were from Sigma. FITC-conjugated goat anti-mouse IgG was from Jackson Immunoresearch Laboratory (West grove, Pa.). Rabbit anti-mouse lymphocyte IgG was the product of Inter-Cell Technologies (Hopewell, N.J.). Hu CD59 cDNA-PUC18 and murine monoclonal antibody (mab) 9E10 against TAG peptide were generous gifts from Dr. A. L. M. Bothwell (Yale Medical School, New Haven, Ct.). Silver stain, Coomasie and BCA protein assay reagents were from Pierce (Rockford, Ill.). All other chemicals were reagent grade or better.

Isolation of rabbit CD59—Rabbit erythrocyte ghost membranes were prepared as described for hu CD59 purification, and suspended to a final volume representing 1.5 times the original volume of packed erythrocytes (Davies et al., (1989) J. Exp. Med. 170, 637–654). The ghost suspension was brought to 150 mM NaCl, 1 mM phenylmethyl sulfony fluoride, and 1-butanol added slowly to 20% vol/vol. Following stirring (3 hr at 4° C.) and centrifugation (30 min, 4° C. at 10,000×g), the butanol-saturated aqueous phase was collected, CHAPS added to final 0.1% (v/v), and dialyzed against 20 mM Tris, 0.1% CHAPS, pH 7.4. The dialyzed extract was applied to 2.5×10-cm DEAE SEPHAROSE Fast Flow column (Sigma) equilibrated in the same buffer and eluted with 500 ml of linear NaCl gradient (0–400 mM). Fractions were tested for MAC inhibitory function, using chicken erythrocyte targets cells as described previously, substituting rb C8 and C9 for hu C8 and C9 (Rollins, S. A. and Sims, P. J. (1990) J. Immunol. 144, 3478–3483). Fractions containing rb MAC inhibitory activity were pooled and NaCl added to final concentration of 300 mM. The pool was applied to 1.6×8-cm phenyl-Sepharose™ column (Sigma) equilibrated with 300 mM NaCl, 0.05% CHAPS, 20 mM Tris, pH 8.0. Following washing with the same solution, protein was eluted with a linear gradient representing 0.05% to 1% CHAPS, 300 mM to 0 mM NaCl, in 20 mM Tris, pH 8.0. The active fractions were pooled and further purified on 0.5×5-cm Mono Q HR™ column (Pharmacia Biotech Inc., Uppsala, Sweden) using a gradient of 0 to 400 mM NaCl in 0.5% CHAPS, 20 mM Tris, pH 7.4. Active fractions were concentrated by step elution on Mono Q™ and further purified by SDS PAGE using a 10% NuPAGE™ gel (Novex, San Diego, Calif.) run under non-reducing conditions. The protein band at 20 kDa (approximately 8 µg total protein from original 300 ml packed rabbit erythrocytes) was eluted from the gel slice into 0.1% CHAPS, 20 mM Tris, pH 7.4 and inhibitory activity of the eluted protein towards rb MAC confirmed by functional assay. All column chromatography procedures were performed at room temperature on a Bio-CAD™ 20 perfusion chromatography workstation (PerSeptive Biosystems, Framingham, Mass.). N-terminal sequence was then obtained through 40 cycles of Edmann degradation (Protein and Carbohydrate Structure Facility, Univ. of Michigan, Ann Arbor, Mich.), yielding S-L-M-C-Y-H-C-L-L-P-S-P-N-C-S-T-V-T-N-C-T-P-N-H-D-A-C-L-T-A-V-S-G-P-R-V-Y-R-Q-C- (Sequence ID No. 16).

Cloning of rabbit CD59 cDNA—Degenerate oligonucleotides were constructed based on peptide sequence and used to amplify a rabbit lymphocyte cDNA library (5'RACE, MARATHON™ Kit, CLONTECH) from which a 200 bp PCR product was obtained. Specific primers based on this 200 bp cDNA were designed and used to amplify the rabbit lymphocyte cDNA library by 3' RACE. Full-length cDNA of rb CD59 was obtained by linking the PCR products from 5' and 3' RACE using PCR. The sequence of this cDNA clone was deposited at GenBank (Accession number: AF040387) and the deduced amino acid sequence of the predicted ORF is shown in FIG. 1. The predicted translation product consists of 124 residues, including a 24-residue signal peptide before the N-terminal Ser[1] of the mature protein. The unusual N-terminal Ser[1] of the mature rb CD59 protein was confirmed at both protein and DNA levels (FIG. 1).

Construction of plasmids encoding rabbit/human CD59 chimeras—The 467 bp insert encoding hu CD59 was released from PUC18 using ECORI restriction sites and subcloned into the ECORI site in pcDNA3 expression vector. The vector with correct CD59 cDNA orientation was selected and used as a template for PCR. A 33 bp oligonucleotide (corresponding to the TAG peptide sequence EQKLISEEDLN (Sequence ID No. 17)) was inserted between the leader sequence of CD59 and the N-terminal amino acid (Leu[1]) of the mature protein using PCR. Rb CD59-TAG in pcDNA3 vector was made by replacing the sequence in hu CD59-TAG pcDNA3 with the sequence encoding mature rb CD59 and the rb CD59 C-terminal signal using HindIII and XbaI sites in pcDNA3. cDNAs encoding the chimeric hu/rb CD59 constructs depicted in FIG. 2 were prepared using PCR amplification by procedures previously described by Zhou, Q., Zhao, J., Hüsler, T., and Sims, P. J. (1996) *Mol. Immunol.* 33, 1127–1134. The pcDNA3 plasmids containing hu CD59 sequence or rb CD59 sequence were used as templates to generate the cDNA encoding chimeric CD59 proteins. The chimeric cDNA was then inserted into pcDNA3 vector using HindIII and XbaI sites. Hu, rb, and hu/rb chimeric CD59-TAG pcDNA3 plasmids were used to transform *E. coli* strain TOP10. Constructs from independent colonies were sequenced in their entirety in both directions by automated DNA sequencing (Applied Biosystems, Inc.) or by dideoxy-sequencing using a sequenase version 2.0 kit. Plasmids containing the desired constructs without nucleotide error were selected and amplified for expression in the SV-T2 cell line.

Expression of CD59 constructs in SV-T2 cells—SV-T2 cells were transfected with hu, rb, or chimeric TAG-CD59 pcDNA3 by electroporation as previously described (Zhou, Q., Zhao, J., Hüsler, T., and Sims, P. J. (1996) *Mol. Immunol.* 33, 1127–1134). After 48 hr, stable transfectants were selected with DMEM complete medium containing 1 mg/ml geneticin for 10 days. If episomal replication in the transfected cells was desired, $8 \times 10^6$ SV-T2 cells were transfected with 120 µg plasmid DNA by electroporation using GENE PULSE™ (Bio-rad) at 360 V and 500 µF (Zhou, Q., Zhao, J., Hüsler, T., and Sims, P. J. (1996) *Mol. Immunol.* 33, 1127–1134). Geneticin-selected cells were stained with mAb 9E10 against TAG epitope followed by FITC-conjugated goat antibody against mouse IgG, and sorted by flow cytometry (FACStar Plus; Becton Dickinson). Individual clones were then obtained by limiting dilution in DMEM containing 0.5 mg/ml geneticin. Comparison was made to clonal cell lines derived by transfection with pcDNA3, lacking insert (vector-only controls).

Measurement of cell surface TAG-CD59—The cell surface expression of each TAG-CD59 construct in transfected SV-T2 cells was quantified by the binding at saturation of mAb 9E10 (against TAG epitope) as previously described by Zhou, Q., Zhao, J., Hüsler, T., and Sims, P. J. (1996) *Mol. Immunol.* 33, 1127–1134. Following growth to near confluence, cells were detached and incubated for 30 min at 23° C. with mAb 9E10 (100 µg/ml) in HBSS containing 1% BSA. After washing with HBSS containing 1% BSA, the cells were incubated (20 min at 23° C.) with FITC conjugated goat anti-mouse IgG at a final concentration of 10 µg/ml. The fluorescence was determined by flow cytometry (FAC-Scan, Becton Dickinson) as described previously by Zhou, Q., Zhao, J., Hüsler, T., and Sims, P. J. (1996) *Mol. Immunol.* 33, 1127–1134.

Assay of MAC inhibitory function—The complement-inhibitory activity of recombinant CD59 expressed on the transfected SV-T2 cells was evaluated by minor modification of methods previously described (Zhou, Q., Zhao, J., Hüsler, T., and Sims, P. J. (1996) *Mol. Immunol.* 33, 1127–1134, and Zhao, J., Rollins, S. A., Maher, S. E., Bothwell, A. L., and Sims, P. J. (1991) *J. Biol. Chem.* 266, 13418–13422). For cell clones expressing each chimeric CD59 construct, huC5b67 was deposited on the plasma membrane and susceptibility to the lytic activity of either hu C8 and C9 or rb C8 and C9 was measured and compared to identically-treated clones expressing wild-type hu or rb CD59. Briefly, SV-T2 cells grown to 80% confluence were washed and loaded with BCECF-AM dye. C5b67 complexes were deposited on the cells using 40% hu C8D serum as complement source. After two washes, the C5b67 cells were incubated in serum-free medium with either 2 µM hu C8 and 5 µM hu C9, or with 4 µM rb C8 and 5 µM rb C9.

MAC-mediated cell lysis was determined from the measured release of BCECF dye from the cytoplasm, with correction for non-specific dye leak from matched controls omitting C8 and C9, as previously described by Zhou, Q., Zhao, J., Hüsler, T., and Sims, P. J. (1996) *Mol. Immunol.* 33, 1127–1134. Under these conditions, MAC-mediated lysis of the vector-only SV-T2 controls not expressing recombinant CD59 ranged from 75–90%.

Results

Cloning of rabbit CD59—The predicted translation product of cDNA encoding rb CD59 consists of 124 residues, including a 24-residue signal peptide, a predicted GPI attachment site, and a 23-residue signal peptide including a transmembrane domain C-terminal to the predicted transamidase cut site (FIG. 1) (Kinoshita, T., Inoue, N., and Takeda, J. (1995) *Adv. Immunol.* 60, 57–103, and Gerber, L. D., Kodukula, K., and Udenfriend, S. (1992) *J. Biol. Chem.* 267, 12168–12173). N-terminal sequencing of protein purified from rabbit erythrocytes and analysis of the signal peptidase cleavage site of the translated cDNA, confirmed that rb CD59 contains an additional Ser residue before the highly-conserved N-terminal $Leu^1$ found in all other CD59 homologues that have been sequenced to date. Therefore, in order to simplify discussion of the aligned residues of hu and rb CD59 in various chimeric constructs, residues of the mature rb CD59 polypeptide have been renumbered commencing with $[N-Ser^0]-Leu^1-Met^2-Cys^3$- etc. (See FIG. 1). All references to amino acids in rb C59 are based on this re-numbering of residues in the mature polypeptide. Whereas $Gly^{76}$ is a predicted transamidase cut site for GPI attachment, the possibility of cleavage at another residue (e.g., $Asp^{74}$) cannot be excluded.

Figure 7A:
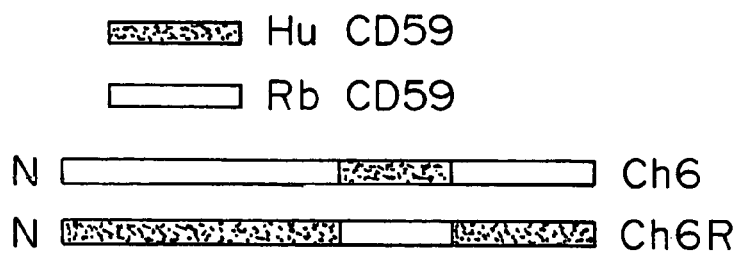
FIGS. 7A, 7B, and 7C are schematics showing the chimeric hu/rb CD59 constructs (FIG. 7A), and graphs of cytolysis (percent release of BCECF Dye versus CD59 per cell (arbitrary fluorescence units) for the human/rabbit chimeras assayed using hu C8/C9 (FIG. 7B) or rb C8/C9 (FIG. 7C).

Species-selective activity of human and rabbit CD59—SV-T2 cell lines expressing various levels of cell surface CD59 (hu or rb) were produced through stable transfection with plasmid pcDNA3-TAG-CD59. Each cell line was then tested for its capacity to resist lysis by C5b-9. As has been previously described, cells transfected to express hu CD59 were nearly completely protected from lysis by hu C5b-9 and this protective effect of hu CD59 was not observed when rb C8 and C9 substituted for hu C8 and C9 in the C5b-9 complex (plotted curves in FIGS. 2B–C). On the other hand, rb CD59 expressed on the surface of this murine cell line conferred a selective resistance to lysis by C5b-9 assembled from rb C8 and C9, whereas virtually no inhibition of the lytic action of MAC was observed when hu C5b-9 components were used. These data confirm that recombinant rb CD59 shows the same homologous species-selective complement inhibitory function as was inferred from the differential susceptibility of rabbit erythrocytes to lysis by human versus rabbit complement (Houle, J. J. and Hoffmann, E. M. (1984) *J. Immunol.* 133, 1444–1452, and Houle, J. J., Hoffmann, E. M., and Esser, A. F. (1988) *Blood* 71, 287–292). As previously noted for the TAG-huCD59 construct (Zhou, Q., Zhao, J., Hüsler, T., and Sims, P. J. (1996) *Mol. Immunol.* 33, 1127–1134), these data also suggest that the TAG-rbCD59 fusion protein retains the properties of native rb CD59 that is expressed in the rabbit erythrocyte membrane Human-rabbit CD59 chimeras—In order to probe which residues of hu CD59 conferred its ability to selectively inhibit lysis by hu C5b-9, chimeric proteins in which segments of the rb and hu CD59 polypeptides were interchanged were constructed. The choice of constructs reflected (i) identity of amino acid residues exposed on the surface of hu CD59 that were not conserved in the aligned polypeptide sequence of rb CD59, where selection was based on the reported solution structure of the glycosylated protein, utilizing surface residues considered not to be occluded by the N-linked carbohydrate (Fletcher, C. M., Harrison, R. A., Lachmann, P. J., and Neuhaus, D. (1994) *Structure* 2, 185–199; Kieffer, B., Driscoll, P. C., Campbell, I. D., Willis, A. C., van der Merwe, P. A., and Davis, S. J. (1994) *Biochemistry* 33, 4471–4482; and Fletcher, C. M., Harrison, R. A., Lachmann, P. J., and Neuhaus, D. (1993) *Protein Sci.* 2, 2015–2027); (ii) an attempt to group these various non-conserved amino acid side chains into contiguously-clustered spatial arrays; and (iii) a consideration of prior data relating to potential identity of the active site residues in hu CD59 as deduced from peptide studies, site-directed mutagenesis in the protein, or from analysis of other CD59 chimeras (Bodian, D. L., Davis, S. J., Morgan, B. P., and Rushmere, N. K. (1997) *J. Exp. Med.* 185, 507–516; Yu, J. H., Dong, S. H., Rushmere, N. K., Morgan, B. P., Abagyan, R., and Tomlinson, S. (1997) *Biochemistry* 36, 9423–9428; Zhou, Q., Zhao, J., Hüsler, T., and Sims, P. J. (1996) *Mol. Immunol.* 33, 1127–1134; Yu, J. H., Abagyan, R., Dong, S. H., Gilbert, A., Nussenzweig, V., and Tomlinson, S. (1997) *J. Exp. Med.* 185, 745–753; Petranka, J., Zhao, J., Norris, J., Tweedy, N. B., Ware, R. E. Sims, P. J., and Rosse, W. F. (1996) *Blood Cells Mol. Dis.* 22, 281–296; and Nakano, Y., Tozaki, T., Kikuta, N., Tobe, T., Oda, E., Miura, N. -H., Sakamoto, T., and Tomita, M. (1995) *Mol. Immunol.* 32, 241–247). Based upon these considerations, six hu/rb CD59 chimeras and, the six complementary rb/hu CD59 chimeras were analyzed and constructed so as to replace the surface-exposed side-chains contributed by residues (i) 8, 10, 12, and 14 (chimeras Ch1 and Ch1R; FIG. 2A); (ii) 5, 37, and 38 (chimeras Ch2 and Ch2R; FIG. 3A); (iii) residues 20, 21, 22, and 41 (chimeras Ch3 and Ch3R; FIG. 4A); (iv) residues 60 and 62 (chimeras Ch4 and Ch4R; FIG. 5A); (v) 29, 30, 60, and 62 (chimeras Ch5 and Ch5R; FIG. 6A); or (vi) residues 44, 48, 49, 51, 52, 55, and 58 (chimeras Ch6 and Ch6R; FIG. 7A). Individual clones expressing each of these recombinant proteins were obtained and the expression level on the cell-surface determined from the N-terminal TAG-epitope common to each construct. In each case, two separate clones were expanded for independent assay of MAC-inhibitory function.

MAC-inhibitory function of recombinant CD59 chimeras—SV-T2 clones expressing the chimeric constructs were analyzed for their capacity to restrict lysis mediated by MAC. The species selectivity of the complement inhibitory function of each construct was tested using hu versus rb C8 and C9 to assemble the C5b-9 complex. In each case, results for the chimeric constructs were compared to those obtained for transfected SV-T2 cells expressing full-length CD59 (hu or rb) and to vector-transfected SV-T2 cells lacking the CD59 insert. As the data of these figures reveal, the species-selective inhibitory function of either hu CD59 or rb CD59 was unaffected by the amino acid substitutions contained in chimeras Ch1/Ch2R, Ch2/Ch2R, Ch4/Ch4R, or Ch5/Ch5R (FIGS. 2B–C, 3B–C, 5B–C and 6B–C). This indicates that residues 1–19, 29, 30, 37, 38, 60, and 62 of the CD59 polypeptide do not directly contribute to its selective avidity for homologous C8 and C9. The results that were obtained for the Ch1/Ch2R chimeras were consistent with recent observations made with hu CD59/Ly6E chimeras, which had suggested that the N-terminal residues of the hu CD59 polypeptide do not contribute to its MAC-inhibitory function (see Discussion).

Figure 7B:
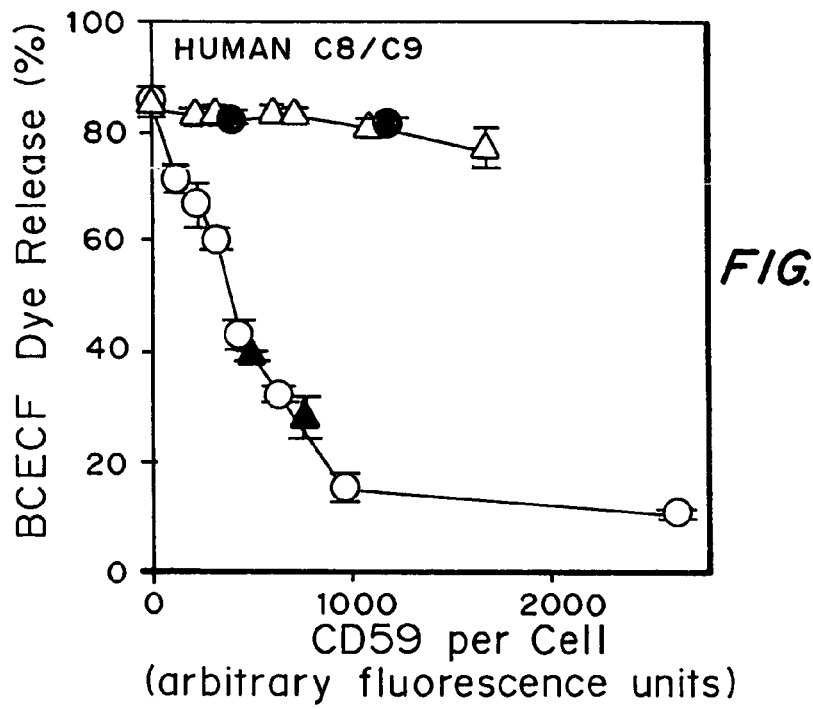
Figure 7C:
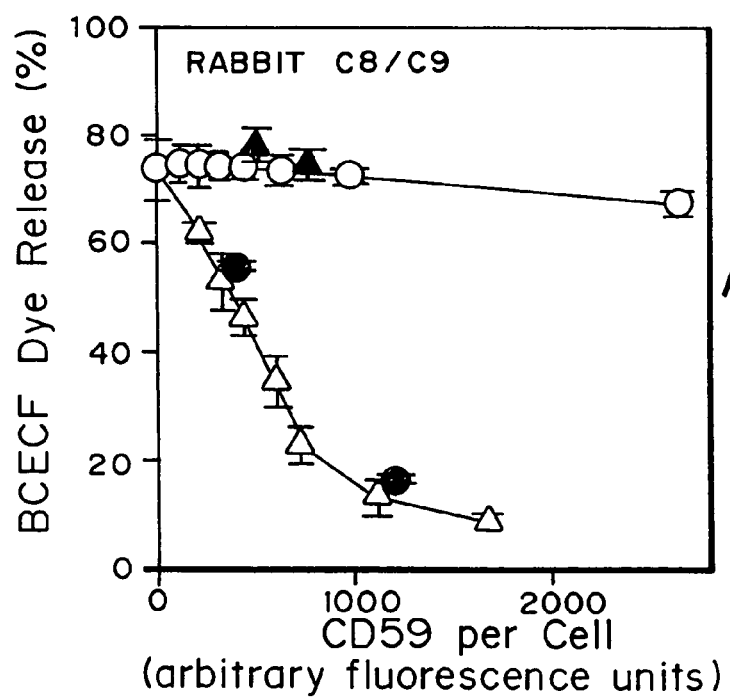

By contrast to results above, substitution of hu CD59 residues 42–58 into rb CD59 resulted in a protein (chimera Ch6) (FIG. 7A) that was functionally indistinguishable from native hu CD59 whereas the complementary construct (rabbit 42–58 substituted in hu CD59, chimera Ch6R) was functionally indistinguishable from rb CD59 (FIGS. 7B–C). These data imply that the amino acid side-chains contributed by residues contained between $Phe^{42}$-$Glu^{58}$ in hu CD59 are responsible for the selective avidity of this complement inhibitor for hu MAC (see Discussion). In the case of chimeras Ch3 and Ch3R (FIGS. 4B–C), a partial loss of CD59's complement-inhibitory function was observed. Replacement of residues 20–22 and 41 in rb CD59 with the corresponding residues from hu CD59 reduced rb CD59's inhibitory activity towards MAC assembled with rb C8/C9, but this substitution did not confer upon rb CD59 the capacity to inhibit hu MAC. Similarly, substitution of hu CD59 residues 20–22 and 41 with the corresponding residues from rb CD59 reduced hu CD59's inhibitory activity towards hu MAC, but this substitution did not confer upon hu CD59 the capacity to inhibit MAC assembled with rb C8/C9.

Summary

The data indicates that residues 42–58 of hu CD59 contain the segment of the protein that is responsible for its species-restricted MAC-inhibitory function. As shown in FIGS. 7B–C, substitution of hu CD59 residues 42–58 into rb CD59 results in a protein that was functionally indistinguishable from hu CD59 whereas the complementary construct (rabbit 42–58 substituted into hu CD59) was functionally indistinguishable from rb CD59. Within this portion of the polypeptide, residues 43, 45, 46, 47, 53, 54, 56 and 57 are identically conserved between human and rabbit. From the solved solution structure of hu CD59, the side-chains of residue 42 and 50 are buried. This indicates that the residues of hu CD59 which dictate its selective ability to bind to hu C8 and C9 are localized to a cluster of amino acid side-chains exposed on the surface of the protein that are contributed by $His^{44}$, $Asn^{48}$, $Asp^{49}$, $Thr^{51}$, $Thr^{52}$, $Arg^{55}$, and $Glu^{58}$. In addition to these residues, data for Ch3/Ch3R (chimeric substitution of residues at position 20, 21, 22 and 41) indicates that the side-chains of one or more of these residues can also influence the species selectivity of hu CD59 (FIGS. 4B–C). Among these residues, it is noteworthy that the side chain of $Lys^{41}$ (replaced by $Arg^{41}$ in rb CD59) projects in close proximity to the side-chain of $His^{44}$ (replaced by $Asp^{44}$ in rb CD59), a residue contained within the functionally dominant segment identified by the Ch6/Ch6R chimeras (cf. FIGS. 7B–C). The relatively conservative Lys→Arg substitution of a side-chain located in proximity to the functionally-dominant region of the protein, may explain why a relatively small loss of activity towards homologous MAC was observed for the Ch3/Ch3R constructs, and why this was not accompanied by a comparable gain in MAC-inhibitory function towards the heterologous complement proteins.

The residues identified in hu CD59 to confer its species-selective interaction with hu C8α and C9 (i.e., $His^{44}$, $Asn^{48}$, $Asp^{49}$, $Thr^{51}$, $Thr^{52}$, $Arg^{55}$, and $Glu^{58}$) form a distinct cluster on the non-glycosylated surface of the protein and would presumably be available for a binding function.

EXAMPLE 2

Demonstration of Role of a Disulfide Bonded Peptide Loop Within Hu C9 in the Species-Selectivity of CD59

Experimental Procedures

Materials—Human complement proteins C5b6, C7, C8, and C9, and human erythrocyte membrane glycoprotein CD59 were purified and assayed as described by Davies, et al. *Immunol. Res.* 12, 258–275 (1993), Wiedmer and Sims, *J. Membr. Biol.* 84, 249–258 (1985), and Wiedmer and Sims, *J. Biol. Chem.* 260, 8014–8019 (1984). Hu C9 peptide 359–384 ([allyl-K]-CLGYHLDVSLAFSEISV-GAEFNKDD-[allyl-C] Sequence ID No. 18), BSA-conjugated hu C9 peptide 359–384, and affinity-purified rabbit IgG against hu C9 peptide 359–384 were custom ordered from Quality Controlled Biochemicals (Hopkinton, Mass.). Full-length cDNA for hu C9 was a generous gift from Dr. J. Tschopp (University of Lausanne, Epalinges, Switzerland) and is described by Dupuis, et al., *Mol. Immunol.* 30, 95–100 (1993). Full length cDNA for rb C9 was isolated and cloned into pSVL as reported by Husler, et al., *J. Biol. Chem.* 270, 3483–3486 (1995). Chicken erythrocytes (chE) were from Cocalico Biologics, Inc. (Reamstown, Pa.); COS-7 cells were from American Tissue Culture Collection (Rockville, Md.); *E. coli* strain DH5α and Opti-MEM I were from Life Technologies Inc. (Gaithersburg, Md.), Dulbecco's Modified Eagle Medium was from Mediatech Inc. (Herndon, Va.), and heat-inactivated fetal bovine serum was from Biocell (Rancho Dominquez, Calif.). Oligonucleotides were synthesized by the Molecular Biology Core Laboratories, Blood Research Institute.

Solutions—MBS: 150 mM NaCl, 10 mM MOPS, pH 7.4; GVBS: 150 mM NaCl, 3.3 mM sodium barbital, 0.15 mM $CaCl_2$ 0.5 mM $MgCl_2$, 0.1% (w/v) gelatin, pH 7.4; GVBE: 150 mM NaCl, 3.3 mM sodium barbital, 10 mM EDTA, 0.1% (w/v) gelatin, pH 7.4.

Construction of chimeric C9 cDNA's—cDNA's coding for hu/rb C9 chimeras were constructed essentially as described by Husler, et al. (1995). In brief, regions of sequence identity were determined from the aligned sequences of rb and hu C9, and used as junctions for chimeric cDNA construction. Based on these alignments, primers for PCR were designed to generate defined segments of rb and hu C9 cDNA's. Primers annealing to 5'- or 3'-untranslated sequence with added XbaI (5'-end) or SacI (3'-end) recognition sites were paired with chimeric primers (28–37 bp in length) and used to generate cDNA fragments that contained the desired overlapping sequence at either the 5'- or 3'-ends. These fragments were gel purified, mixed at a 1:1 molar ratio, and used in a second amplification with primers located in the 5'- and 3'-untranslated region to produce full length chimeric C9 cDNA's. Fragments were cloned into the XbaI/SacI sites of pSVL for mammalian expression. PCR fidelity was confirmed by sequencing 3'-coding sequence in each construct, starting from the stop codon and continuing through all junctions of rabbit and human sequence. In certain cases, chimeric constructs were further modified by site directed mutagenesis.

Site Directed Mutagenesis—C9 cDNA in pSVL served as a template for site-directed mutagenesis using the Chameleon mutagenesis kit (Stratagene, La Jolla, Calif.). Mutagenesis was performed using 0.25 pmol of template plasmid, 25 pmol of mutagenic primer and 25 pmol of selection primer, the latter chosen to modify SalI, ScaI, or XhoI restriction sites unique to pSVL. The resulting mutagenized plasmids were subject to a minimum of two rounds of selection by restriction digest, and then transformed in *E. coli* XL1-Blue (Stratagene) for single colony isolation and plasmid purification. In all cases, mutations were confirmed by double stranded sequencing of each purified plasmid.

Transfection of COS-7 cells—Plasmid DNA used in transfections was obtained from purification over QIAGEN-TIPS™ (Qiagen Inc., Chatsworth, Calif.). COS-7 cells were transfected using DEAE-dextran, then cultured for 24 h in Dulbecco's Modified Eagle Medium (Mediatech Inc., Herndon, Va.) supplemented with 10% fetal bovine serum, after which this medium was replaced by Opti-MEM I (Life Technologies, Inc., Gathersburg, Md.). Cell supernatants were harvested after 48–65 h, PMSF (1 mM), benzamidine (1 mM) and EDTA (10 mM) were added and the supernatants concentrated at 4° C. (Centricon 30, Amicon).

Immunoblotting—C9 in the COS-7 supernatants was analyzed by quantitative dot blotting using murine monoclonal antibody P9-2T as described by Husler, et al. (1995).

Biotin-CD59—CD59 was biotinylated by incubation (1 h, room temperature) with a 20-fold molar excess of NHS-LC-biotin in 10 mM MOPS, 0.1% Nonidet P-40, pH 9.0 followed by exhaustive dialysis against charcoal, as described by Chang, et al. *J. Biol. Chem.* 269, 26424–26430 (1994).

Analysis of the inhibitory function of CD 59 towards recombinant C9 constructs—Hemolytic activity of each C9 construct was assayed using as target cells chE that were reconstituted with purified hu CD59, as described by Husler, et al., (1995). chE were washed extensively and suspended in GVBS, and the membrane C5b67 complex assembled by mixing cells ($1.4\times10^9$/ml) with C5b6 (13 µg/ml) followed by addition of C7 (1 µg/ml). After 10 min., the C5b67 chE were diluted to $1.4\times10^8$/ml in GVBE and incubated (10 min. 37° C.) with 0 or 750 ng/ml CD59. In each case, the final concentration of Nonidet P-40 was less than 0.002% (v/v). After washing in ice-cold GVBE, $2.8\times10^8$ of these cells were incubated (37° C.) in a total volume of 100 µl with 1 ng rb C8 plus, between zero and 50 ng of recombinant C9, serially diluted in Opti-MEM I. Hemolysis was determined after 30 minutes at 37° C., with correction for nonspecific lysis, determined in the absence of C9. In each experiment, the inhibitory activity of CD59 towards each recombinant C9 construct was determined from the reduction in complement lysis of those cells reconstituted with CD59, versus the identically-treated cells omitting CD59, measured at the midpoint of the C9 titration (i.e., 50% hemolysis). In order to directly compare results obtained in experiments performed on different days, data for each recombinant C9 construct were normalized to results obtained in each experiment with hu C9.

CD59 binding to hu C9 peptide 359–384—The specific binding of CD59 to hu C9-derived peptide 359–384 was measured by microtiter plate assay with biotin-CD59, according to modification of published methods of Chang, et al. (1994) and Husler, et al. (1995). Briefly, the BSA-peptide conjugate was adsorbed to 96 well polyvinyl microplates by overnight coating at 5 µg/ml in 0.1 M sodium bicarbonate, pH 8.5. After blocking with 1% (w/v) BSA, wells were washed and incubated (4 hrs., 37° C.) with between 0.5 and 1 µg/ml biotin-CD59. After washing, the bound biotin-CD59 was detected with Vectastain (Vector Labs, Burlingame, Calif.), developed by addition of p-nitrophenyl phosphate (2 mg/ml) and optical density recorded at 405 nm (VMaxMicroplate Reader, Molecular Devices, Inc.). In all experiments, correction was made for background adsorption of biotin-CD59 to BSA-coated wells (no peptide) and for nonspecific binding of biotin-CD59 to peptide, determined in the presence of a 20-fold excess of unlabeled CD59. As a positive control for specific binding, comparison was made in each experiment to wells coated with 2 µg/ml hu C9. The capacity of monospecific antibody against hu C9 peptide 359–384 to compete specific binding of C59 was determined by prior incubation of the BSA-peptide-coated wells with antibody (2 hrs., between 0 and 100 µg/ml LgG) before addition of biotin-CD59.

Inhibition of MAC lysis by antibody against hu C9 peptide 359–384—The capacity of antibody against hu C9 peptide 359–384 to inhibit MAC was determined by hemolytic assay, using the chE target cells described above, omitting CD59. In these experiments, between 0 and 1 mg/ml Fab of antibody against hu C9 peptide 359–384 (or, non-immune antibody control) was added with recombinant C9 (hu, rb, or chimeric), and complement-specific lysis determined.

Results

C9 chimeras were constructed in which the segment of C9 corresponding to the putative CD59 binding site (residues 334–415 in hu C9; FIG. 9A were interchanged between hu and rb C9. These chimeric proteins were then tested for hemolytic activity and for their sensitivity to inhibition by membrane CD59 (FIG. 9B). Substitution of hu C9 residues 334–415 into rb C9 (chimera #1) resulted in a protein that was indistinguishable from hu C9 in its sensitivity to inhibition by CD59. Conversely, when this same segment of hu C9 was replaced by the corresponding rb C9 sequence (chimera #8), the resulting chimera was indistinguishable from rb C9 and virtually unaffected by the presence of membrane CD59. In these experiments, MAC was assembled using hu C5b67 and rb C8 so as to circumvent known inhibitory interaction of CD59 with hu C8 (Rollins, et al. *J. Immunol.* 146, 2345–2351 (1991), Ninomiya and Sims *J. Biol. Chem.* 267, 13675–13680 (1992).

Figure 10:
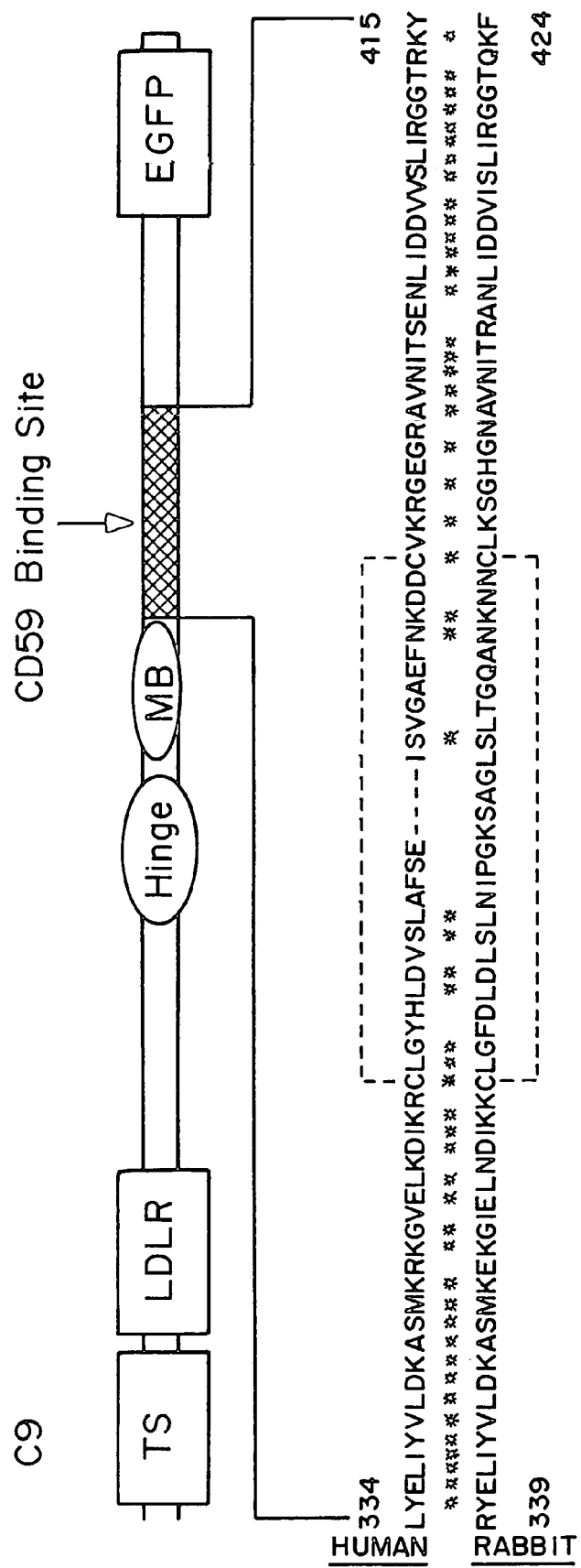
FIG. 10 is a schematic representation of the segment of hu C9 identified as containing the CD59 binding site, which according to the proposed domain structure includes: thrombospondin type 1 (TS), LDL-receptor (LDLR), hinge (Hinge), membrane binding (MB), and epidermal growth factor precursor (EGFP) domains. Shaded segment indicates residues 334–415 of hu C9, spanning the putative CD59 binding site. The amino acid sequence of this peptide segment (Sequence ID No. 14) is given below, and is shown in an alignment with rb C9 (Sequence ID No. 15) (alignment done for full-length polypeptides with the PALIGN program in PCGENE). Asterisks indicate sequence identity. Dotted lines indicate the Cys 359/384 disulfide of hu C9 and the assumed corresponding internal disulfide in rb C9. Residue numbers refer to the mature proteins.
Figure 11:
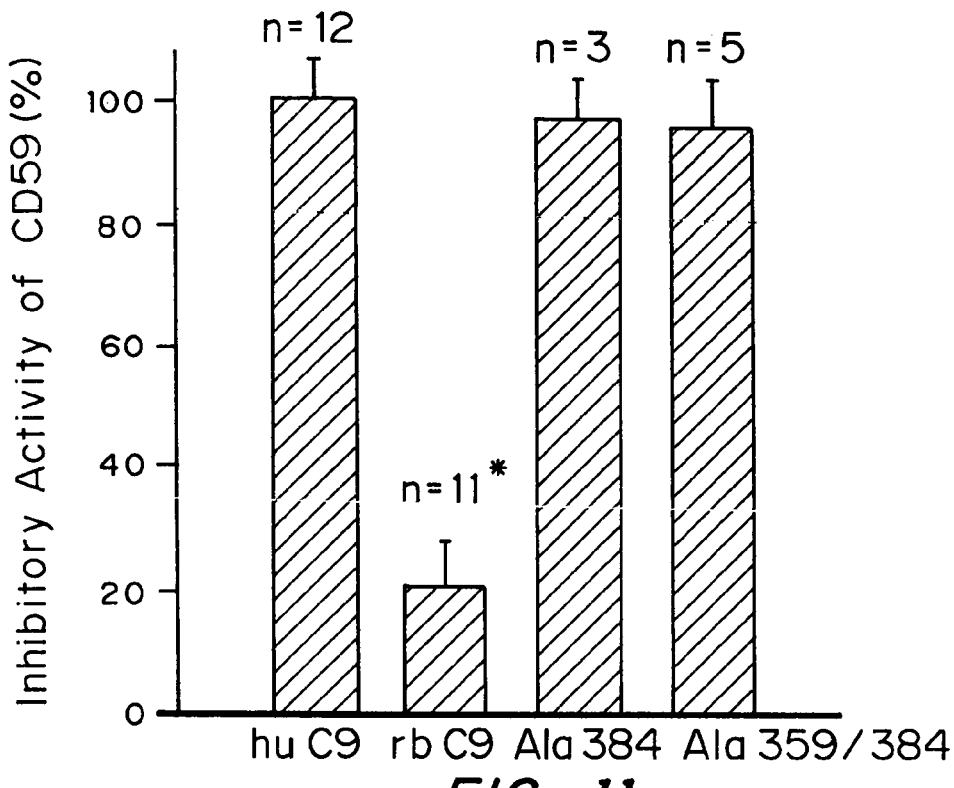
FIG. 11 is a graph showing percent inhibitory activity of CD59 is unaffected by disruption of the Cys 359/384 disulfide. Recombinant hu C9 was expressed with Cys→Ala mutation at either residue 384 or at both residues 359/384, and analyzed as described in FIG. 9B. Inhibitory activity of CD 59 measured as hemolytic function of each recombinant C9 is expressed as a percentage, relative to that measure for wild-type hu C9 (ordinate). Error bars denote mean+S.D., n, indicates number of independent experiments; asterisks indicate significance (p, 0.001) compared to hu C9. Hu C9 and rb C9 denote the wild type human and rabbit proteins, respectively.

As depicted in FIG. 10, the segment of hu C9 shown to bind CD59 is immediately C-terminal to the putative membrane-spanning domain of the protein, and corresponds to a segment of polypeptide exhibiting particularly low sequence conversation when hu C9 is aligned to C9 of rabbit or other non-primate species. The most prominent divergence of sequence occurs between two cysteines (Cys359–Cys384 in hu C9) that are conserved in the human and rabbit proteins. In hu C9, these cysteines have been shown to form an intrachain disulfide bond (below), as reported by Schaller, et al. *J. Protein Chem.* 13, 472–473 (1994).

In order to further localize the segment of hu C9 recognized by CD59 and to determine the specific contribution of residues spanning the Cys359/384 disulfide, a series of hu/rb C9 chimeras was constructed by interchanging segments of corresponding hu and rb C9 sequences internal to residues 334–415. Each of these chimeric proteins was expressed and analyzed for MAC hemolytic function, and for sensitivity to inhibition by membrane CD59. All resulting hu/rb C9 chimeras were functionally active as determined by hemolytic titration against chE containing membrane C5b-8. As shown in FIGS. 9A–B, analysis of CD59-inhibitory activity towards each of these proteins revealed inhibition of MAC lytic activity by CD59 was unaffected by replacement of all residues N-terminal to Cys359 of hu C9 with corresponding rabbit sequence (chimera #2), whereas replacement of all residues C-terminal to residue 358 of hu C9 with corresponding rabbit sequence (chimera #3) resulted in a protein indistinguishable from rb C9 and only weakly inhibited by CD59. Consistent with the results for chimeras #1–3, substitution of hu C9 residues 359–415 into the corresponding segment of otherwise rb C9 (chimera #4) resulted in a protein that was indistinguishable from hu C9, suggesting that this polypeptide segment of hu C9 (residues 359–415) contains the binding site for CD59.

To further resolve the segment of hu C9 required for species-selective interaction with CD59, additional chimeras were constructed further truncating the segment of human sequence substituted into rb C9 (chimera #5–7). Data for these chimeras revealed that whereas human residues 359–391 conferred full recognition by CD59 (chimera #5), hu C9 residues 392–415 failed to confer any recognition by CD59 (chimera #5), hu C9 residues 392–415 failed to confer any recognition by CD59 when inserted into an otherwise rb C9 (chimera #6). Truncation of the inserted segment of hu C9 sequence from 359–391 (chimera #5) to 359–384 (chimera #7) was accompanied by a small but significant reduction in inhibition of MAC lytic activity by CD59. These results imply that CD59 directly interacts with the segment of hu C9 contained between residues 359–391, with the peptide segment spanning the intrachain Cys359/384 disulfide substantially contributing to this interaction.

CD59's interaction with hu C9 was abrogated by replacement of sequence spanning this putative CD59 recognition domain with corresponding rabbit sequence (chimeras #8–12). Replacement of hu C9 residues 334–415 with corresponding rabbit sequence (chimera #8) completely eliminated hu-selective interaction with CD59, as anticipated for results obtained for the complementary construct, chimera #1. Nevertheless, when the segment of rb-derived sequence substituted into otherwise hu C9 was further truncated, the resulting chimeras (chimeras #9–12) retained a surprising degree of sensitivity to the inhibitory effects of CD59, characteristic of hu C9. Thus substitution of rabbit sequence for the residues internal to Cys359–384 of hu C9 (chimera #12) did not significantly diminish CD59's capacity to inhibit the lytic activity of C9, while C-terminal extension of the segment of rabbit sequence to residue 415 (chimera #9) did not completely eliminate interaction with CD59. Taken together with results for chimeras #1–5, these data indicate that whereas hu C9 residues 359–391 alone are sufficient to confer recognition by CD59, segments of the polypeptide immediately flanking this segment significantly contribute to the extent to which this binding site is expressed.

The Cys359/384 disulfide in hu C9 has recently been reported to be highly labile and subject to spontaneous reduction in the native protein, as reported Hatanaka, et al., *Biochim. Biophys. Acta Protein Struct. Mol. Enzymol.* 1209, 117–122 (1994). Since the data suggested that residues internal to Cys359/384 contribute in-large-part to species-selective recognition by CD59, the extent to which the CD59 recognition site in C9 is affected by disruption of this bond was examined. Mutant hu C9 was expressed with Ala substitutions at Cys359 and Cys384 and tested for hemolytic activity and for sensitivity to inhibition by CD59. As revealed by data of FIG. 6, disruption of this disulfide bond did not significantly affect the hemolytic activity of the protein nor the capacity of CD59 to specifically inhibit C9 lytic activity. This suggests that the segment of hu C9 forming the CD59 binding site is either conformationally constrained independent of the Cys359–384 disulfide, or, that this binding site is expressed in the primary structure of hu C9, independent of protein folding.

Figure 12:
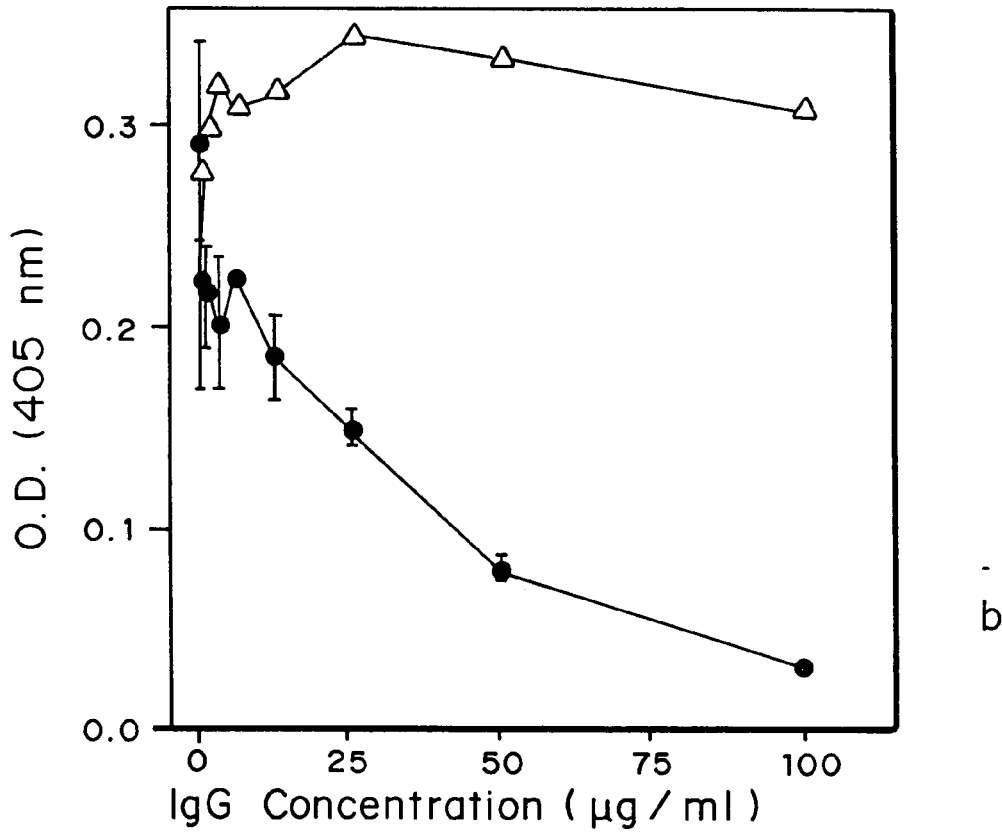
FIG. 12 is a graph showing CD59 specifically binds hu C9 peptide 359–384. Microplates were coated with hu C9 peptide 359–384 coupled to BSA, and specific binding of biotin-CD59 determined in the presence of affinity-purified antibody against hu C9 residues 359–384 (●), or non-immune IgG (Δ) (micrograms/ml IgG concentration indicated on abscissa). All data were corrected for nonspecific binding of CD59, determined in presence of 20-fold excess of unlabeled CD59. Ordinate denotes absorbance at 405 nm, with correction for nonspecific background. Error bars denote mean+S.D. Data of a single experiment, representative of three so performed.

In order to confirm that the peptide segment spanning hu C9 359–384 can itself mediate interaction with CD59, this 26 residue peptide was synthesized, coupled to BSA, and analyzed for CD59 binding, using biotin-CD59 conjugate in a micro plate assay. As demonstrated by FIG. 12, biotin-CD59 specifically bound to C9 peptide 359–384, and this binding was inhibited by excess unlabeled CD59 or by antibody directed against the peptide.

Figure 13A:
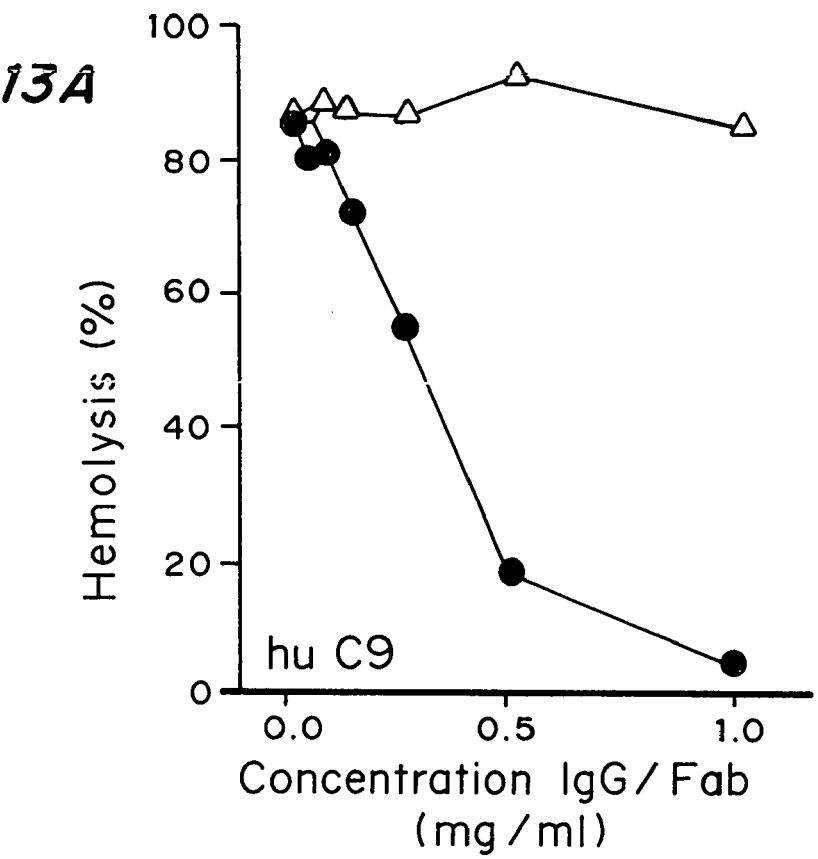
FIGS. 13A, 13B, 13C and 13D are graphs showing the inhibition of C9-dependent hemolysis by antibody against C9-peptide 359–384. Fab of antibody against hu C9 peptide 359–384 (●) was tested for its capacity to inhibit the hemolytic activity of recombinant hu C9 (FIG. 13A), hu/rb C9 chimera #7 (FIG. 13B), recombinant rb C9 (FIG. 13C), or hu/rb C9 chimera #12 (FIG. 13D). Residues of human (H) and rabbit (R) sequence in each C9 chimera are indicated in FIG. 9A. Also shown is data for non-immune antibody (Δ) (final concentrations indicated on abscissa). In all experiments, C5b-8 chE lacking CD59 served as target cells and hemolysis measured with correction for nonspecific lysis. Data of single experiment, representative of three similar experiments.
Figure 13B:
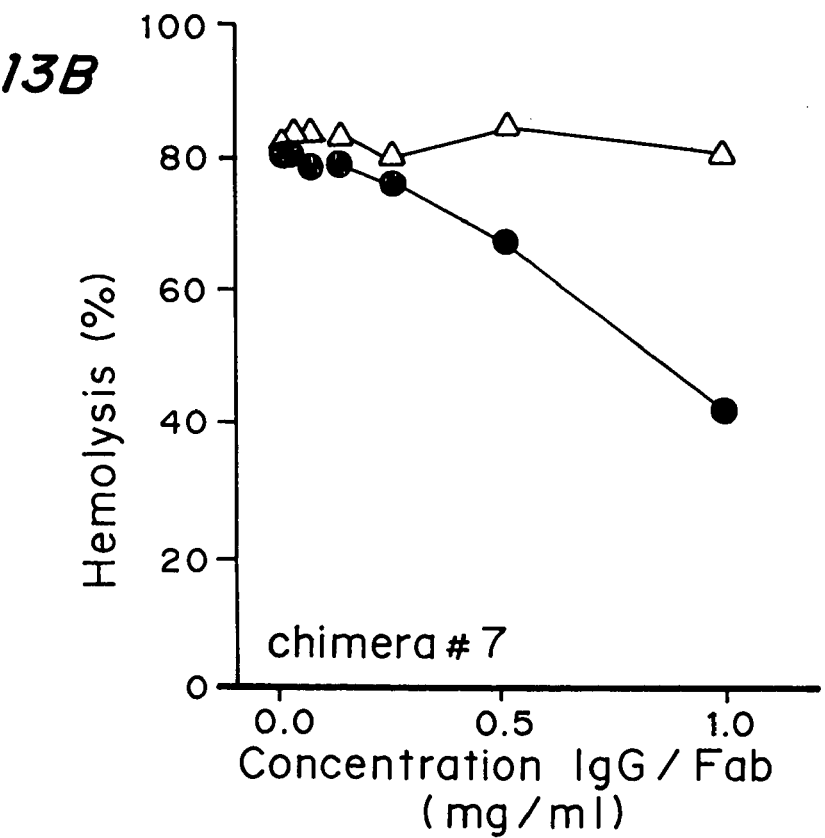
Figure 13C:
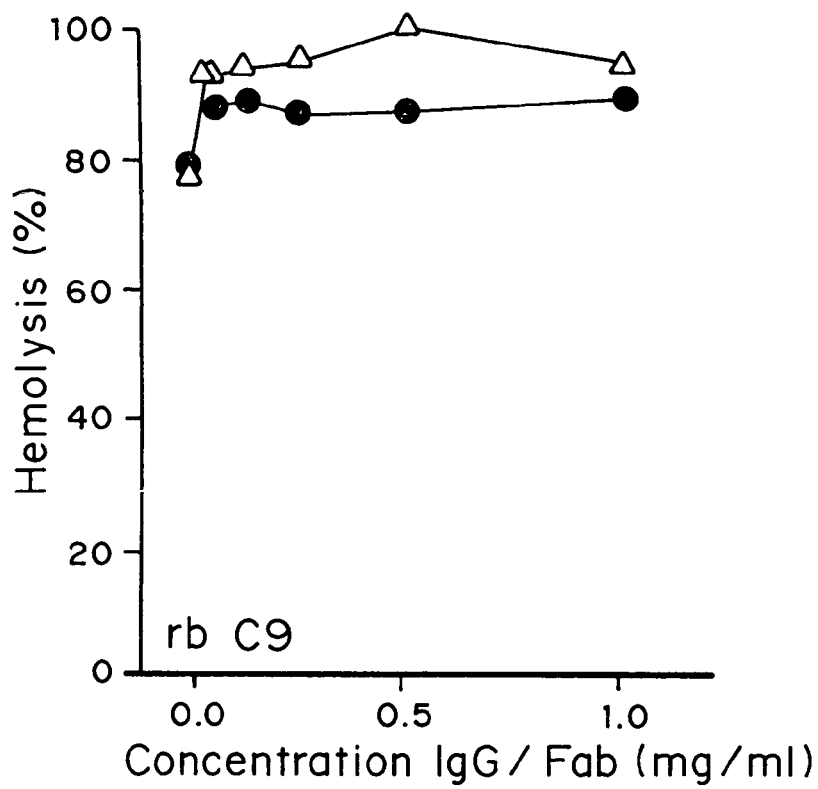
Figure 13D:
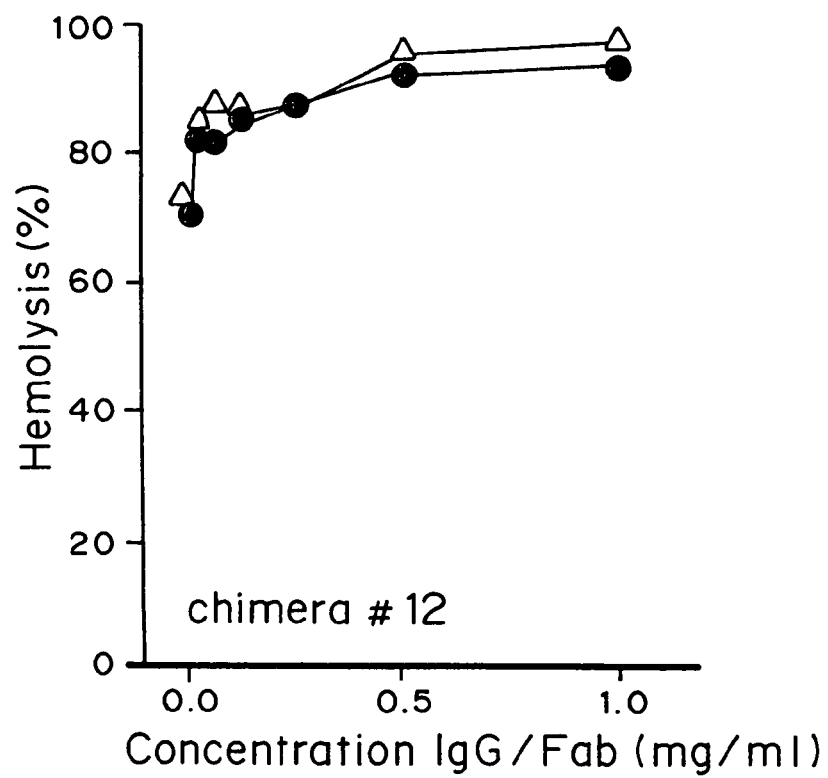

CD59 is known to bind to C9 after C9 incorporates into the C5b-9 complex, and through this interaction inhibit propagation of membrane-inserted C9 polymer, limiting lytic activity of MAC. In order to confirm the importance of the peptide segment recognized by CD59 to MAC assembly, Fab of antibody raised against the hu C9 peptide 359–384 was tested for its capacity to inhibit the hemolytic activity of the hu C5b-9 complex, under the same condition used to evaluate the inhibitory function of CD59. As shown by the data of FIGS. 13A–D, this Fab inhibited hemolytic activity of hu C9 (FIG. 13A) and C9 chimera #7 (representing rb C9 containing hu C9 residues 359–384, FIG. 13B), but had no effect on the hemolytic activity of either rb C9 (FIG. 13C) or chimera #12 (representing substitution of the corresponding segment of rb C9 residues into hu C9; FIG. 13D).

The experiments show that hu C9 residues 359–391 promote CD59 binding, and that this segment of hu C9 contributes to the species-selective regulation of MAC function, providing an initial clue to the structural motif(s) through which this inhibitor selectively regulates the lytic activity of hu C5b-9 complex. These data further indicate that the capacity of CD59 to optimally interact with this segment of hu C9 is significantly influenced by residues immediately C-terminal to this segment of the C9 polypeptide.

Whereas the data establish that residues internal to Cys359–Cys384 contribute to recognition by CD59, the disulfide bond between these two Cys is apparently not required either for maintenance of C9's hemolytic activity within MAC, or, for normal regulation of that activity by membrane CD59. These conclusions derived by Cys/Ala mutagenesis in recombinant hu C9 (FIG. 6) are consistent with previous reports indicating: (i) the intrinsic liability of the Cys 359–384 disulfide in C9 purified from hu plasma, where spontaneous reduction of this bond did not appear to alter C9 hemolytic activity, and (ii) that a specific CD59 binding site is retained in reduced and carboxymethylated hu C9, in hu C9-derived peptide fragments, and can be demonstrated for *E. coli* fusion proteins contains hu C9-derived sequence spanning residues 359–384. This suggests that the CD59 binding site expressed by this segment of hu C9 reflects interactions between amino acid side chains that do not require formation of the Cys 359/Cys 384 disulfide bond.

As noted above, chimeras generated by substituting limited segments of hu C9 into rb C9 revealed that the segment of hu C9 between 359–384 uniquely conferred recognition by CD59, and that this interaction was enhanced by C-terminal extension of human sequence to residue 391 (cf. Chimeras #1–7; FIGS. 9A–B). Surprisingly, chimeras generated by replacing these same segments of hu C9 with corresponding rb C9 sequence did not exhibit a complementary decrease in interaction with CD59, except when the segment of rb-derived sequence replaced in hu C9 residues spanning 334–415 (cf. Chimeras #8–12; FIGS. 9A–B).

I claim:

1. A compound that specifically inhibits the formation of the human C5b-9 complex, said compound comprising a peptidomimetic or a peptide of less than forty amino acid residues and having the structure and function of human CD59 amino acid residues 42–58 of SEQ ID NO:3, the peptidomimetic or peptide binding specifically to human C9 at amino acid residues 26–51 of SEQ ID NO:14.

2. The compound of claim 1, wherein the compound is a chimeric peptide that comprises the amino acids 42 to 58 of the human sequence CD59 in SEQ ID NO:3.

3. The compound of claim 1, wherein the compound is a covalently cyclized peptide comprising human CD59 amino acid residues 42 to 58 in SEQ ID NO:3.

4. The compound of claim 1, wherein the compound is a peptide that comprises amino acid residues 42 to 58 of human CD59 in SEQ ID NO:3.

5. The compound of claim 1, wherein the compound is a peptidomimetic compound comprising the side chains of human CD59 amino acid residues His[44], Asn[48], Asp[49], Thr[51], Thr[52], Arg[55], and Glu[58] of SEQ ID NO:3 in an equivalent spatial orientation and alignment to that presented on the surface of human CD59.

6. The compound of claim 5, wherein the spatial orientation and alignment of the side chains of His[44], Asn[48], Asp[49], Thr[51], Thr[52], Arg[55], and Glu[58] of SEQ ID NO:3 in the compound are equivalent to the spatial orientation and alignment deduced by NMR structure determination.

7. A composition comprising a compound that specifically inhibits the formation of the human C5b-9 complex, said compound comprising a peptidomimetic or a peptide of less than forty amino acid residues and having the structure and function of human CD59 amino acid residues 42–58 of SEQ ID NO:3, the peptidomimetic or peptide binding specifically to amino acid residues 26 to 51 of human C9 in SEQ ID NO:14, and a pharmaceutically acceptable carrier for administration to patients in need thereof.

8. The composition of claim 7, wherein the compound is a chimeric peptide that comprises the amino acids 42 to 58 of the human sequence CD59 in SEQ ID NO:3.

9. The composition of claim 7, wherein the compound is a covalently cyclized peptide comprising human CD59 amino acid residues 42 to 58 in SEQ ID NO:3.

10. The composition of claim 7, wherein the compound is a peptide that comprises amino acid residues 42 to 58 of human CD59 in SEQ ID NO:3.

11. A method for inhibiting human C5b-9 complex assembly comprising administering an effective amount of a composition comprising a peptidomimetic or a peptide of less than forty amino acid residues and having the structure and function of human CD59 amino acid residues 42–58 in SEQ ID NO:3, the peptidomimetic or peptide binding specifically to human C9 at amino acid residues 26–51 of SEQ ID NO:14.

12. The method of claim 11, wherein the compound is a chimeric peptide that comprises the amino acids 42 to 58 of the human sequence of CD59 in SEQ ID NO:3.

13. The method of claim 11, wherein the compound is a covalently cyclized peptide comprising human CD59 amino acid residues 42 to 58 in SEQ ID NO:3.

14. The method of claim 11, wherein the compound is a peptide that comprises amino acid residues 42 to 58 of human CD59 in SEQ ID NO:3.

15. The method of claim 11, wherein the composition further comprises a pharmaceutically acceptable carrier for administration to patients in need thereof.

16. The method of claim 11, wherein the composition is administered to a patient in need of suppression of complement-mediated inflammation.

17. The method of claim 11, wherein the compound is a peptidomimetic comprising the side chains of human CD59 amino acid residues $His^{44}$, $Asn^{48}$, $Asp^{49}$, $Thr^{51}$, $Thr^{52}$, $Arg^{55}$, and $Glu^{58}$ of SEQ ID NO:3 in the spatial orientation and alignment of human CD59.

18. The method of claim 17, wherein the spatial orientation and alignment of the side chains of $His^{44}$, $Asn^{48}$, $Asp^{49}$, $Thr^{51}$, $Thr^{52}$, $Arg^{55}$, and $Glu^{58}$ of SEQ ID NO:3 in the compound are deduced by NMR structure determination.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 127 amino acids
      (B) TYPE: amino acid
      (C) STRANDEDNESS: single
      (D) TOPOLOGY: linear (ii) MOLECULE TYPE: peptide (iii) HYPOTHETICAL: NO (vi) ORIGINAL SOURCE:
      (A) ORGANISM: Human (xi) SEQUENCE DESCRIPTION: SEQ ID NO:1:

```
Gly Ile Gln Gly Gly Ser Val Leu Phe Gly Leu Leu Val Leu Ala
1               5                   10                  15

Val Phe Cys His Ser Gly His Ser Leu Gln Cys Tyr Asn Cys Pro Asn
                20                  25                  30

Pro Thr Ala Asp Cys Lys Thr Ala Val Asn Cys Ser Ser Asp Phe Asp
            35                  40                  45

Ala Cys Leu Ile Thr Lys Ala Gly Leu Gln Val Tyr Asn Lys Cys Trp
        50                  55                  60

Lys Phe Glu His Cys Asn Phe Asn Asp Val Thr Thr Arg Leu Arg Glu
65                  70                  75                  80
```

```
Asn Glu Leu Thr Tyr Tyr Cys Cys Lys Lys Asp Leu Cys Asn Phe Asn
                85                  90                  95

Glu Gln Leu Glu Asn Gly Gly Thr Ser Leu Ser Glu Lys Thr Val Leu
            100                 105                 110

Leu Leu Val Thr Pro Phe Leu Ala Ala Ala Trp Ser Leu His Pro
        115                 120                 125

(2) INFORMATION FOR SEQ ID NO:2:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Rabbit (xi) SEQUENCE DESCRIPTION: SEQ ID NO:2:

Met Thr Ser Arg Gly Val His Leu Leu Leu Arg Leu Phe Leu Leu
1               5                   10                  15

Ala Val Phe Tyr Ser Ser Asp Ser Ser Leu Met Cys Tyr His Cys Leu
            20                  25                  30

Leu Pro Ser Pro Asn Cys Ser Thr Val Thr Asn Cys Thr Pro Asn His
            35                  40                  45

Asp Ala Cys Leu Thr Ala Val Ser Gly Pro Arg Val Tyr Arg Gln Cys
    50                  55                  60

Trp Arg Tyr Glu Asp Cys Asn Phe Glu Phe Ile Ser Asn Arg Leu Glu
65                  70                  75                  80

Glu Asn Ser Leu Lys Tyr Asn Cys Cys Arg Lys Asp Leu Cys Asn Gly
            85                  90                  95

Pro Glu Asp Asp Gly Thr Ala Leu Thr Gly Arg Thr Val Leu Leu Val
            100                 105                 110

Ala Pro Leu Leu Ala Ala Ala Arg Asn Leu Cys Leu
        115                 120

(2) INFORMATION FOR SEQ ID NO:3:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Human (xi) SEQUENCE DESCRIPTION: SEQ ID NO:3:

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
            35                  40                  45
```

```
Asp Val Thr Thr Arg Leu Arg Glu Asn Glu Leu Thr Tyr Tyr Cys Cys
            50                  55                  60

Lys Lys Asp Leu Cys Asn Phe Asn Glu Gln Leu Glu Asn
 65              70                  75
```

(2) INFORMATION FOR SEQ ID NO:4:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Baboon (xi) SEQUENCE DESCRIPTION: SEQ ID NO:4:

```
Leu Gln Cys Tyr Asn Cys Pro Asn Pro Thr Thr Asn Cys Lys Thr Ala
 1               5                  10                  15

Ile Asn Cys Ser Ser Gly Phe Asp Thr Cys Leu Ile Ala Arg Ala Gly
             20                  25                  30

Leu Gln Val Tyr Asn Gln Cys Trp Lys Phe Ala Asn Cys Asn Phe Asn
                 35                  40                  45

Asp Ile Ser Thr Leu Leu Lys Glu Asn Glu Leu Gln Tyr Phe Cys Cys
            50                  55                  60

Lys Glu Asp Leu Cys Asn Gly Gln Leu Glu Asn
 65              70                  75
```

(2) INFORMATION FOR SEQ ID NO:5:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: African green monkey (xi) SEQUENCE DESCRIPTION: SEQ ID NO:5:

```
Leu Gln Cys Tyr Asn Cys Pro Asn Pro Thr Thr Asp Cys Lys Thr Ala
 1               5                  10                  15

Ile Asn Cys Ser Ser Gly Phe Asp Thr Cys Leu Ile Ala Arg Ala Gly
             20                  25                  30

Leu Gln Val Tyr Asn Gln Cys Trp Lys Phe Ala Asn Cys Asn Phe Asn
                 35                  40                  45

Asp Ile Ser Thr Leu Leu Lys Glu Ser Glu Leu Gln Tyr Phe Cys Cys
            50                  55                  60

Lys Lys Asp Leu Cys Asn Phe Asn Glu Gln Leu Glu Asn
 65              70                  75
```

(2) INFORMATION FOR SEQ ID NO:6:

(i) SEQUENCE CHARACTERISTICS:
        (A) LENGTH: 77 amino acids
        (B) TYPE: amino acid
        (C) STRANDEDNESS: single

```
          (D) TOPOLOGY: linear (ii) MOLECULE TYPE: peptide (iii) HYPOTHETICAL: NO (vi) ORIGINAL SOURCE:
           (A) ORGANISM: Owl monkey (xi) SEQUENCE DESCRIPTION: SEQ ID NO:6:

Leu Gln Cys Tyr Ser Cys Pro Tyr Pro Thr Thr Gln Cys Thr Met Thr
1               5                  10                  15

Thr Asn Cys Thr Ser Asn Leu Asp Ser Cys Leu Ile Ala Lys Ala Gly
            20                  25                  30

Ser Arg Val Tyr Tyr Arg Cys Trp Lys Phe Glu Asp Cys Thr Phe Ser
        35                  40                  45

Arg Val Ser Asn Gln Leu Ser Glu Asn Glu Leu Lys Tyr Tyr Cys Cys
    50                  55                  60

Lys Lys Asn Leu Cys Asn Phe Asn Glu Ala Leu Glu Asn
65                  70                  75

(2) INFORMATION FOR SEQ ID NO:7:

(i) SEQUENCE CHARACTERISTICS:
           (A) LENGTH: 77 amino acids
           (B) TYPE: amino acid
           (C) STRANDEDNESS: single
           (D) TOPOLOGY: linear (ii) MOLECULE TYPE: peptide (iii) HYPOTHETICAL: NO (vi) ORIGINAL SOURCE:
           (A) ORGANISM: Marmoset (xi) SEQUENCE DESCRIPTION: SEQ ID NO:7:

Leu Gln Cys Tyr Ser Cys Pro Tyr Ser Thr Ala Arg Cys Thr Thr Thr
1               5                  10                  15

Thr Asn Cys Thr Ser Asn Leu Asp Ser Cys Leu Ile Ala Lys Ala Gly
            20                  25                  30

Leu Arg Val Tyr Tyr Arg Cys Trp Lys Phe Glu Asp Cys Thr Phe Arg
        35                  40                  45

Gln Leu Ser Asn Gln Leu Ser Glu Asn Glu Leu Lys Tyr His Cys Cys
    50                  55                  60

Arg Glu Asn Leu Cys Asn Phe Asn Gly Ile Leu Glu Asn
65                  70                  75

(2) INFORMATION FOR SEQ ID NO:8:

(i) SEQUENCE CHARACTERISTICS:
           (A) LENGTH: 75 amino acids
           (B) TYPE: amino acid
           (C) STRANDEDNESS: single
           (D) TOPOLOGY: linear (ii) MOLECULE TYPE: peptide (iii) HYPOTHETICAL: NO (xi) SEQUENCE DESCRIPTION: SEQ ID NO:8:

Leu Gln Cys Tyr Asn Cys Ser His Ser Thr Met Gln Cys Lys Thr Ser
1               5                  10                  15

Thr Ser Cys Thr Ser Asn Leu Asp Ser Cys Leu Ile Ala Lys Ala Gly
            20                  25                  30
```

```
Ser Gly Val Tyr Asn Lys Cys Trp Lys Phe Asp Asp Cys Ser Phe Lys
        35                  40                  45

Arg Ile Ser Asn Gln Leu Ser Glu Thr Gln Leu Lys Tyr His Cys Cys
        50                  55                  60

Lys Lys Asn Leu Cys Asn Val Asn Lys Gly Ile
65                  70                  75

(2) INFORMATION FOR SEQ ID NO:9:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Pig (xi) SEQUENCE DESCRIPTION: SEQ ID NO:9:

Leu Gln Cys Tyr Asn Cys Ile Asn Pro Ala Gly Ser Cys Thr Xaa Xaa
1               5                   10                  15

Met Asn Cys Ser Tyr Asn Gln Asp Ala Cys Ile Phe Val Xaa Ala Val
                20                  25                  30

Pro Pro Lys Thr
        35

(2) INFORMATION FOR SEQ ID NO:10:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Sheep (xi) SEQUENCE DESCRIPTION: SEQ ID NO:10:

Leu Gln Cys Tyr Ser Cys Ile Asn Gln Val Asp Cys Thr Ser Val Ile
1               5                   10                  15

Asn Cys Thr Xaa Asn Gln Asp Ala Cys Leu Tyr
                20                  25

(2) INFORMATION FOR SEQ ID NO:11:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Rabbit (xi) SEQUENCE DESCRIPTION: SEQ ID NO:11:
```

-continued

```
Ser Leu Met Cys Tyr His Cys Leu Leu Pro Ser Pro Asn Cys Ser Thr
 1               5                  10                  15

Val Thr Asn Cys Thr Pro Asn His Asp Ala Cys Leu Thr Ala Val Ser
            20                  25                  30

Gly Pro Arg Val Tyr Arg Gln Cys Trp Arg Tyr Glu Asp Cys Asn Phe
        35                  40                  45

Glu Phe Ile Ser Asn Arg Leu Glu Glu Asn Ser Leu Lys Tyr Asn Cys
50                      55                  60

Cys Arg Lys Asp Leu Cys Asn Gly Pro Glu Asp Asp Gly
65                  70                  75
```

(2) INFORMATION FOR SEQ ID NO:12:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Rat (xi) SEQUENCE DESCRIPTION: SEQ ID NO:12:

```
Leu Arg Cys Tyr Asn Cys Leu Asp Pro Val Ser Ser Cys Lys Thr Asn
 1               5                  10                  15

Ser Thr Cys Ser Pro Asn Leu Asp Ala Cys Leu Val Ala Val Ser Gly
            20                  25                  30

Lys Gln Val Tyr Gln Gln Cys Trp Arg Phe Ser Asp Cys Asn Ala Lys
        35                  40                  45

Phe Ile Leu Ser Arg Leu Glu Ile Ala Asn Val Gln Tyr Arg Cys Cys
50                      55                  60

Gln Ala Asp Leu Cys Asn Lys Ser Phe Glu Asp Lys Pro Asn Asn
65                  70                  75
```

(2) INFORMATION FOR SEQ ID NO:13:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Mouse (xi) SEQUENCE DESCRIPTION: SEQ ID NO:13:

```
Leu Thr Cys Tyr His Cys Phe Gln Pro Val Val Ser Ser Cys Asn Met
 1               5                  10                  15

Asn Ser Thr Cys Ser Pro Asp Gln Asp Ser Cys Leu Tyr Ala Val Ala
            20                  25                  30

Gly Met Gln Val Tyr Gln Arg Cys Trp Lys Gln Ser Asp Cys His Gly
        35                  40                  45

Glu Ile Ile Met Asp Gln Leu Glu Glu Thr Lys Leu Lys Phe Arg Cys
50                      55                  60

Cys Gln Phe Asn Leu Cys Asn Lys Ser Asp
```

(2) INFORMATION FOR SEQ ID NO:14:

(i) SEQUENCE CHARACTERISTICS:
        (A) LENGTH: 82 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Human (xi) SEQUENCE DESCRIPTION: SEQ ID NO:14:

```
Leu Tyr Glu Leu Ile Tyr Val Leu Asp Lys Ala Ser Met Lys Arg Lys
1               5                  10                  15

Gly Val Glu Leu Lys Asp Ile Lys Arg Cys Leu Gly Tyr His Leu Asp
            20                  25                  30

Val Ser Leu Ala Phe Ser Glu Ile Ser Val Gly Ala Glu Phe Asn Lys
        35                  40                  45

Asp Asp Cys Val Lys Arg Gly Glu Gly Arg Ala Val Asn Ile Thr Ser
    50                  55                  60

Glu Asn Leu Ile Asp Asp Val Val Ser Leu Ile Arg Gly Gly Thr Arg
65                  70                  75                  80

Lys Tyr
```

(2) INFORMATION FOR SEQ ID NO:15:

(i) SEQUENCE CHARACTERISTICS:
        (A) LENGTH: 86 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Rabbit (xi) SEQUENCE DESCRIPTION: SEQ ID NO:15:

```
Arg Tyr Glu Leu Ile Tyr Val Leu Asp Lys Ala Ser Met Lys Glu Lys
1               5                  10                  15

Gly Ile Glu Leu Asn Asp Ile Lys Lys Cys Leu Gly Phe Asp Leu Asp
            20                  25                  30

Leu Ser Leu Asn Ile Pro Gly Lys Ser Ala Gly Leu Ser Leu Thr Gly
        35                  40                  45

Gln Ala Asn Lys Asn Asn Cys Leu Lys Ser Gly His Gly Asn Ala Val
    50                  55                  60

Asn Ile Thr Arg Ala Asn Leu Ile Asp Asp Val Ile Ser Leu Ile Arg
65                  70                  75                  80

Gly Gly Thr Gln Lys Phe
                85
```

(2) INFORMATION FOR SEQ ID NO:16:

(i) SEQUENCE CHARACTERISTICS:
        (A) LENGTH: 40 amino acids
        (B) TYPE: amino acid

```
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:16:

Ser Leu Met Cys Tyr His Cys Leu Leu Pro Ser Pro Asn Cys Ser Thr
1               5                   10                  15

Val Thr Asn Cys Thr Pro Asn His Asp Ala Cys Leu Thr Ala Val Ser
                20                  25                  30

Gly Pro Arg Val Tyr Arg Gln Cys
            35                  40

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:17:

Glu Gln Lys Leu Ile Ser Glu Glu Asp Leu Asn
1               5                   10

(2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:18:

Lys Cys Leu Gly Tyr His Leu Asp Val Ser Leu Ala Phe Ser Glu Ile
1               5                   10                  15

Ser Val Gly Ala Glu Phe Asn Lys Asp Asp Cys
                20                  25
```